(12) United States Patent
Gyakushi et al.

(10) Patent No.: US 8,796,354 B2
(45) Date of Patent: Aug. 5, 2014

(54) DENTAL ADHESIVE COMPOSITION

(75) Inventors: Hidetoshi Gyakushi, Tsukuba (JP);
Takeshi Suzuki, Sakuragawa (JP);
Mihoko Kajikawa, Tsukuba (JP);
Hideki Kazama, Tsuchiura (JP)

(73) Assignee: Tokuyama Dental Corporation, Taito-ku, Tokyo (JP)

( * ) Notice: Subject to any disclaimer, the term of this patent is extended or adjusted under 35 U.S.C. 154(b) by 0 days.

(21) Appl. No.: 12/999,464

(22) PCT Filed: Jul. 22, 2009

(86) PCT No.: PCT/JP2009/063121
§ 371 (c)(1),
(2), (4) Date: Dec. 16, 2010

(87) PCT Pub. No.: WO2010/010901
PCT Pub. Date: Jan. 28, 2010

(65) Prior Publication Data
US 2011/0098375 A1    Apr. 28, 2011

(30) Foreign Application Priority Data
Jul. 25, 2008 (JP) .................... 2008-191542

(51) Int. Cl.
*C08L 43/02* (2006.01)

(52) U.S. Cl.
USPC ............ 523/118; 523/113; 523/115; 523/116

(58) Field of Classification Search
USPC ....................................... 523/118
See application file for complete search history.

(56) References Cited

U.S. PATENT DOCUMENTS

| | | | | |
|---|---|---|---|---|
| 3,256,233 | A * | 6/1966 | Hahn et al. ............... | 523/201 |
| 3,259,601 | A * | 7/1966 | Protzek et al. ............ | 524/710 |
| 3,296,175 | A * | 1/1967 | Hahn et al. ............... | 524/820 |
| 3,377,382 | A * | 4/1968 | Elmquist .................. | 564/291 |
| 3,642,710 | A * | 2/1972 | Keen et al. ............... | 528/336 |
| 3,779,970 | A * | 12/1973 | Evani et al. .............. | 524/523 |
| 4,259,075 | A | 3/1981 | Yamauchi et al. | |
| 4,259,117 | A | 3/1981 | Yamauchi et al. | |
| 4,368,043 | A | 1/1983 | Yamauchi et al. | |
| 4,539,382 | A | 9/1985 | Omura et al. | |
| 4,612,384 | A | 9/1986 | Omura et al. | |
| 4,650,847 | A | 3/1987 | Omura et al. | |
| 5,154,762 | A * | 10/1992 | Mitra et al. .............. | 106/35 |
| 5,866,630 | A * | 2/1999 | Mitra et al. .............. | 523/118 |
| 5,925,690 | A * | 7/1999 | Fuchigami et al. ........ | 523/118 |
| 6,217,644 | B1 | 4/2001 | Matsunae et al. | |
| 6,583,197 | B1 * | 6/2003 | Wada et al. .............. | 522/84 |
| 6,613,439 | B1 | 9/2003 | Goebel | |
| 7,041,714 | B2 * | 5/2006 | Takeshita et al. ......... | 523/118 |
| 2006/0270751 | A1 * | 11/2006 | Thalacker et al. ........ | 523/116 |
| 2010/0261144 | A1 | 10/2010 | Fujinami et al. | |
| 2010/0317762 | A1 * | 12/2010 | Matsushige et al. ....... | 523/118 |

FOREIGN PATENT DOCUMENTS

| | | | | |
|---|---|---|---|---|
| EP | 1066813 | A2 * | 1/2001 | ............ A61K 6/083 |
| EP | 2 123 246 | A1 | 11/2009 | |
| EP | 2123246 | A1 * | 11/2009 | ............... A61K 6/00 |
| EP | 2 206 488 | A1 | 7/2010 | |
| JP | 52-113089 | A | 9/1977 | |
| JP | 53-113843 | A | 10/1978 | |
| JP | 56-136865 | A | 10/1981 | |
| JP | 56136865 | A * | 10/1981 | ................. C09J 3/14 |
| JP | 58-021687 | A | 2/1983 | |
| JP | 9-263604 | A | 10/1997 | |
| JP | 10-236912 | A | 9/1998 | |
| JP | 2000-086421 | A | 3/2000 | |
| JP | 2001-072523 | A | 3/2001 | |
| JP | 2002-047355 | A | 2/2002 | |
| JP | 2002-327023 | A | 11/2002 | |
| JP | 2008-201726 | A | 9/2008 | |
| WO | WO 2008/102489 | A1 | 8/2008 | |
| WO | WO 2009/051045 | A1 | 4/2009 | |
| WO | WO 2009/063967 | A1 | 5/2009 | |

OTHER PUBLICATIONS

International Search Report (PCT/ISA/210) issued on Aug. 18, 2009, by Japanese Patent Office as the International Searching Authority or International Application No. PCT/JP2009/063121.
The Extended European Search Report issued on Dec. 10, 2013, by the European Patent Office in corresponding European Patent Application No. 09800415.3. (7 pages).

* cited by examiner

*Primary Examiner* — James J Seidleck
*Assistant Examiner* — Peter A Salamon
(74) *Attorney, Agent, or Firm* — Buchanan Ingersoll & Rooney PC

(57) ABSTRACT

[Problems] A dental adhesive composition containing an acid group-containing polymerizable monomer, that can be used as a dental adhesive material or a primer. The dental adhesive composition has excellent durability of adhesion exhibiting further improved adhering strength and durability of adhesion enabling teeth to be more strongly adhered to a composite resin or a prosthetic over extended periods of time.
[Means for Solution] The dental adhesive composition contains a polymerizable monomer and ions of an element of the Group IV as basic components, at least 10 mass % of the polymerizable monomer being a polymerizable monomer having a hydrogenphosphate diester group, such as bis(2-methacryloyloxyethyl)hydrogenphosphate or 2-methacryloyloxyethylphenyl hydrogenphosphate, and the content of ions of the element of the Group IV such as titanium ions or zirconium ions in the composition being 0.1 to 1.0 in terms of mole ratio to the hydrogenphosphate diester groups of the polymerizable monomer that has the hydrogenphosphate diester group.

6 Claims, No Drawings

DENTAL ADHESIVE COMPOSITION

TECHNICAL FIELD

This invention relates to a dental adhesive composition useful as a primer or adhesive material for adhering together a tooth and a dental restorative that comprises a metal, organic high molecular material, ceramics or a composite material thereof in the field of dental therapy.

BACKGROUND ART

A tooth that is damaged by caries, abrasion, etc. is, usually, directly restored by using a composite resin from the standpoint of aesthetic appearance, simple and quick operation when a cavity that is formed therein is still in the initial to intermediate stage and is small. On the other hand, a relatively large cavity is restored, usually, by using a prosthetic made of a metal, ceramics or a dental resin.

The dental restorative such as the composite resin or the prosthetic basically has no adhesive property to the tooth. Usually, therefore, use is made of an adhesive material comprising a polymerizable monomer composition for adhering the dental restorative to the tooth. The polymerizable monomer used for the adhesive material, usually, comprises a methacrylate type monomer as a chief component but its adhering force to the tooth is not satisfactory. When adhering the composite resin, for instance, the adhering strength is not, in many cases, large enough to overcome the internal stress that generates at the time when the composite resin is cured, i.e., is not large enough to overcome the tensile stress that occurs in the interface between the tooth and the composite resin. Besides, the adhering strength is not, in many cases, large enough to withstand the force produced by occlusion. In order to improve the adhering strengths of these adhesive materials, therefore, the following pretreatments have been conducted for the tooth surfaces at the time of using the adhesive materials.

1) Application of a pretreating material for etching a hard tooth (enamel comprising chiefly hydroxyapatite); and
2) Application of a pretreating material called primer for accelerating the permeation of the adhesive material into the tooth.

Under such circumstances, attempts have been made to develop a dental adhesive material containing a polymerizable monomer having adhesive property to the tooth in order to attain a larger adhering strength while reducing complexity of operation. For instance, higher adhering strengths have been expressed by using, at least as part of the polymerizable monomer component, a polymerizable monomer (hereinafter referred to as acid group-containing polymerizable monomer) containing an acid group such as phosphoric acid group or carboxylic acid group having high affinity to the tooth (hydroxyapatite or collagen) (patent document 1 and patent document 2).

There has also been reported that the adhering strength can be improved by using a phosphoric monoester monomer as an acid group-containing polymerizable monomer in the form of a metal salt with calcium or the like (patent document 3). Attempts have also been made to add a polyvalent metal ion-eluting filler to an adhesive material or primer that contains an acid group-containing polymerizable monomer and water to further improve its curability by polymerization (patent documents 4 to 7). Here, the polyvalent metal ion-eluting filler stands for a filler such as fluoroaluminosilicate glass that elutes out metal ions in an acidic solution. As polyvalent metal ions eluted out therefrom, there can be exemplified ions of such metals as alkaline earth metals, aluminum, etc. As the polyvalent metal ion-eluting filler, there has also been used a filler by substituting titanium or zirconium for part of the aluminum. However, there is found no Working Example that really uses ions of an element of the Group IV, and the amount of adding them has not been concretely taught, either. The reason why the adhesive material containing the polyvalent metal ion-eluting filler exhibits improved adhering strength is attributed to that when the adhesive material cures, the polymerizable monomer containing the acid group-containing polymerizable monomer undergoes the polymerization and, at the same time, polyvalent metal ions eluted out from the polyvalent metal ion-eluting filler form a salt with the acid group of the acid group-containing polymerizable monomer, whereby ionic crosslinking takes place enabling the strength of the cured body to be enhanced.

PRIOR ART DOCUMENTS

Patent Documents

Patent document 1: JP-A-52-113089
Patent document 2: JP-A-58-21687
Patent document 3: JP-A-53-113843
Patent document 4: JP-A-9-263604
Patent document 5: JP-A-10-236912
Patent document 6: JP-A-2001-72523
Patent document 7: JP-A-2000-86421
Patent document 8: JP-A-2008-201726

OUTLINE OF THE INVENTION

Problems that the Invention is to Solve

An adhesive composition (adhesive material or primer) containing an acid group-containing polymerizable monomer gives a larger adhering strength than that of the adhesive composition without containing the above monomer and, further, provides a function for demineralization the tooth owing to the action of the acid group enabling the operation of adhesion to be simplified. The adhering strength, however, is not still large enough since a very large adhering strength is required between the tooth and the dental restorative as described above. According to the above-mentioned invention that improves the adhering strength by using a calcium salt of the phosphoric monoester monomer, further, there have been exemplified elements of the Group IV such as titanium or zirconium as elements for forming metal salts. Even by using the phosphoric monoester monomer and the metal salt of the element of the Group IV, however, the adhering strength is not still satisfactory (patent document 3).

Similarly, an adhesive material containing a polyvalent metal ion-eluting filler gives improved adhesive property which, however, is not of a sufficiently practical level. In the adhesive material containing the polyvalent metal ion-eluting filler, if it is attempted to obtain a large adhering strength by developing a sufficient degree of ionic crosslinking, then the kind and amount of metal ions eluted out from the polyvalent metal ion-eluting filler that is used play very important roles. If the eluted ions are chiefly monovalent metal ions or divalent metal ions such as calcium ions, then the adhesive property is not sufficiently improved. Besides, if the metal ions are eluted out in too large amounts (Example 9 of patent document 7), water-resisting property of the adhesive material after cured greatly decreases. Therefore, though a considerably large adhering force may be obtained immediately after the curing, durability of sufficiently large adhesion cannot be maintained over long periods of time.

Under such circumstances, the present inventors have proposed an invention for improving the adhesive property to the tooth by mixing specific polyvalent metal ions and the phosphoric acid type polymerizable monomer at a specific mixing ratio as one package and by developing ionic crosslinking (patent document 8). The adhesive material of this type is stored in the form of one package. While being stored, the polyvalent metal ions and the phosphoric acid type polymerizable monomer form ionic crosslinking; i.e., crosslinking density is increased to greatly increase the adhering strength. Still, however, the adhering strength is not fully satisfactory for practical use, and a further improvement is required. It is, therefore, a serious problem to develop a dental adhesive composition which has more improved adhering strength and durability of adhesion, which more strongly adheres a composite resin or a prosthetic to the tooth, and which exhibits excellent durability of adhesion over extended periods of time.

Means for Solving Problems

In order to solve the above technical problems, the present inventors have conducted keen study. As a result, the inventors have discovered that the above problems can be solved if ions of an element of the Group IV is made present in a specified amount in a liquid of a dental adhesive composition that contains, at least as part of a polymerizable monomer component, a polymerizable monomer containing a hydrogenphosphate diester group (hereinafter referred to as phosphoric diester polymerizable monomer), and have completed the present invention.

According to the present invention, there is provided a dental adhesive composition containing:
(A) a polymerizable monomer that contains not less than 10 mass % of a polymerizable monomer that has a hydrogenphosphate diester group; and
(B) ions of an element of the Group IV;
  wherein the content of the ions of the element of the Group IV is 0.1 to 1.0 in terms of a mole ratio to the hydrogenphosphate diester groups of the polymerizable monomer (A-1) that has the hydrogenphophate dieter group.
In the above dental adhesive composition, it is desired that:
(1) Ions of the element of the Group IV are titanium ions;
(2) A polymerization initiator (C) is, further, contained;
(3) The composition is acidic;
(4) Fluoride ions (D) are contained at a molar ratio of 0.4 to 4.0 to the ions of the element of the Group IV; and
(5) Water (E) is, further, contained.

According to the present invention, there is further provided a method of producing a dental adhesive composition by mixing together:
(A) a polymerizable monomer that contains not less than 10 mass % of a polymerizable monomer that has a hydrogenphosphate diester group;
(E) water; and
($B_{alk}$) a metal alkoxide of an element of the Group IV in such an amount that the amount of ions of the element of the Group IV is 0.1 to 1.0 in terms of a mole ratio to the hydrogenphosphate diester groups of the polymerizable monomer (A-1) that has the hydrogenphosphate diester group;
  wherein the polymerizable monomer (A-1) that has the hydrogenphosphate diester group is mixed to the metal alkoxide of the element of the Group IV ($B_{alk}$), first, and is, thereafter, mixed to water (E).

Effects of the Invention

As compared to the conventional adhesive materials containing an acid group-containing polymerizable monomer and a polyvalent metal ion-eluting filler, the dental adhesive composition of the present invention is capable of further greatly improving the adhering strength to the tooth. That is, when used as an adhesive material for adhering the dental restorative and the tooth together, the dental adhesive material of the invention has very excellent adhering strength for both the dentin and the enamel so as to highly withstand the tensile stress that develops in the interface to the composite resin and, further, has very excellent adhering strength against the force produced by occlusion. As will be described later, this fact is presumably due to that the ionic crosslinking of a polymer formed by the polymerization of ionic bond of an acid group of the phosphoric diester polymerizable monomer and an ion of an element of the Group IV is more highly dense than the conventional ionic crosslinking formed by an acid group of an acid group-containing polymerizable monomer and a polyvalent metal ion eluted out from a polyvalent metal ion-eluting filler. By utilizing the above large adhering strength, therefore, the dental adhesive composition of the present invention is useful as an adhesive material featuring high water-resisting property and excellent durability of adhesion enabling the tooth to be adhered to the dental restorative such as a composite resin or a prosthetic maintaining stability for extended periods of time. The dental adhesive composition of the invention is, further, useful as a primer that is applied to the surface of the tooth prior to using the adhesive material for attaining the adhesion.

MODE FOR CARRYING OUT THE INVENTION

The dental adhesive composition of the invention uses (A) a polymerizable monomer and (B) ions of an element of the Group IV as basic components.
(A) Polymerizable Monomer.

The polymerizable monomer (A) is a compound that has, in a molecule thereof, a polymerizable unsaturated group such as acryloyl group, methacryloyl group, acrylamide group, methacrylamide, vinyl group, allyl group, ethynyl group or styryl group. From the standpoint of curing rate, in particular, it is desired that the compound has the acryloyl group, methacryloyl group, acrylamide group or methacrylamide group and, most desirably, has the acryloyl group or methacryloyl group.
(A-1) Phosphoric Diester Polymerizable Monomer.

In the present invention, it is important that not less than 10 mass % of (A) the whole polymerizable monomer component is (A-1) a phosphoric diester polymerizable monomer. The phosphoric diester polymerizable monomer not only exhibits a high demineralization action for the dentin but also exhibits a high bonding force to the tooth and, further, excels in the ability for forming ionic bond with an ion of the element of the Group IV that is present making it possible to obtain a particularly large adhering strength. A large adhering strength of the present invention is not attained even by using a polymerizable monomer having such a phosphoric acid group as phosphinic acid group, phosphonic acid group, hydrogen phosphonate monoester group or dihydrogen phosphate monoester group though they are the acid groups derived from the same phosphoric acid.

As the compounds that can be favorably used as (A-1) the phosphoric diester polymerizable monomer, there can be exemplified the polymerizable monomers represented by the following general formulas:

[Chemical 1]

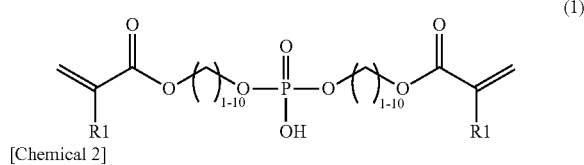

(1)

[Chemical 2]

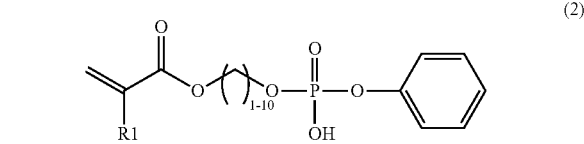

(2)

wherein $R^1$ is a hydrogen atom or a methyl group.

These compounds can be used alone or as a mixture of two or more kinds. Among them, it is desired to use a compound represented by the formula (I) having two polymerizable functional groups and, most desirably, to use a bis[2-(meth)acryloyloxyethyl]hydrogenphosphate.

The content of (A-1) the phosphoric diester polymerizable monomer must not be less than 10 mass % of the polymerizable monomer. Here, however, the polymerizable monomer may all be the phosphoric diester polymerizable monomer only.

(A-2) Phosphoric Acid Group-Containing Polymerizable Monomer.

The dental adhesive composition of the present invention may contain a polymerizable monomer having an acid group derived from (A-2) a phosphoric acid (hereinafter referred to as phosphoric acid group-containing polymerizable monomer) other than (A-1) the phosphoric diester polymerizable monomer. Examples of the phosphoric acid group-containing polymerizable monomer include bis(2-methacryloxyethyl)phosphinic acid, bis(3-methacryloxypropyl)phosphinic acid, and bis(4-methacryloxybutyl)phosphinic acid, which are having a phosphinic acid group; 3-methacryloxypropylphosphonic acid, 2-methacryloxyethoxycarbonylmethylphosphonic acid, 4-methacryloxybutoxycarbonylmethylphosphonic acid and 6-methacrloxyhexyloxycarbonylmethylphosphonic acid, which are having a phosphonic acid group; and 3-methacryloxyethylphosphonic mono(methacryloxyethyl)ester and 3-methacryloxyethylphosphonic monophenyl ester which are having a hydrogenphosphonate monoester group.

(A-3) Non-Acid Group-Containing Polymerizable Monomer.

From the standpoint of adjusting the permeability of the adhesive into the tooth and improving the strength of the cured body, further, it is desired to also use (A-3) a polymerizable monomer without acid group (hereinafter referred to as non-acid group-containing polymerizable monomer). Even when the non-acid group-containing polymerizable monomer is also used, it is necessary to use (A-1) the phosphoric diester polymerizable monomer in an amount of not less than 10 mass % and, more preferably, in a range of 15 to 60 mass % in the whole polymerizable monomer from the standpoint of improving the adhering strength to both the enamel and the dentin. If the phosphoric diester polymerizable monomer is blended in small amounts, the adhering strength to the enamel tends to decrease. If it is blended in too large amounts, on the other hand, the adhering strength to the dentin tends to decrease.

Any known non-acid group-containing polymerizable monomer (A-3) can be used without limitation provided it has at least one polymerizable unsaturated group (mentioned above) in a molecule thereof. Concrete examples include mono(meth)acrylate type monomers such as methyl(meth)acrylate (stands for methyl acrylate or methyl methacrylate, hereinafter the same), ethyl(meth)acrylate, glycidyl(meth)acrylate, 2-cyanomethyl(meth)acrylate, benzyl(meth)acrylate, polyethylene glycol mono(meth)acrylate, allyl(meth)acrylate, 2-hydroxyethyl(meth)acrylate, glycidyl(meth)acrylate, 3-hydroxypropyl(meth)acrylate, glycerylmono(meth)acrylate, and 2-(meth)acryloxyethylacetyl acetate; and polyfunctional (meth)acrylate type monomers such as ethylene glycol di(meth)acrylate, diethylene glycol di(meth)acrylate, triethylene glycol di(meth)acrylate, nonaethylene glycol di(meth)acrylate, propylene glycol di(meth)acrylate, dipropylene glycol di(meth)acrylate, 2,2'-bis[4-(meth)acryloyloxyethoxyphenyl]propane, 2,2'-bis[4-(meth)acryloyloxyethoxyethoxyphenyl]propane, 2,2'-bis{4-[3-(meth)acryloyloxy-2-hydroxypropoxy]phenyl}propane, 1,4-butanedioldi(meth)acrylate, 1,6-hexanedioldi(meth)acrylte, trimethylolpropanetri(meth)acrylate, urethane(meth)acrylate, and epoxy(meth)acrylate.

As the non-acid group-containing polymerizable monomer (A-3), there can be, further, used polymerizable monomers other than those (meth)acrylate type monomers that are described above. As the other non-acid group-containing polymerizable monomers, there can be exemplified fumaric ester compounds such as dimethyl fumarate, diethyl fumarate and diphenyl fumarate; styrenes such as styrene, divinylbenzene, α-methylstyrene, α-methylstyrene dimer and α-methylstyrene derivative; and allyl compounds such as diallyl phthalate, diallyl terephthalate, diallyl carbonate and allyl diglycol carbonate. These non-acid group-containing polymerizable monomers can be used alone or being mixed together in two or more kinds.

Further, when there are used water and a highly hydrophobic polymerizable monomer, it is desired to also use a water-soluble non-acid group-containing polymerizable monomer such as 2-hydroxyethyl(meth)acrylate or 3-hydroxypropyl(meth)acrylate from the standpoint of preventing the separation of water and maintaining stable adhering strength as a homogeneous composition.

(B) Ions of an Element of the Group IV.

It is essential that the dental adhesive composition of the present invention contains (B) ions of an element of the Group IV in a specified amount together with the polymerizable monomer component. Upon curing the polymerizable monomer in the copresence of ions of the element of the Group IV, the dental adhesive composition exhibits greatly increased adhering strength, improved water-resisting property and excellent durability of adhesion.

As the ions of the element of the Group IV, there can be concretely exemplified titanium ions, zirconium ions and hafnium ions. Among them, titanium ions can be exemplified as ions of the element of the Group IV having higher effect. Ions of the elements of the Group IV may be used in two or more kinds being mixed together.

The content of ions of the element of the Group IV present in the dental adhesive composition is 0.1 to 1.0 and, preferably, 0.2 to 0.6 in terms of a mole ratio to the hydrogenphosphate diester groups in the phosphoric diester polymerizable monomer. If the content of ions of the element of the Group IV present in the composition becomes smaller than 0.1 in terms of a mole ratio to the hydrogenphosphate diester groups, the crosslinking density due to the ionic bond of the ions of the element of the Group IV and the phosphoric diester polymerizable monomer decreases, and adhesive property is not exhibited to a sufficient degree. If the mole ratio becomes larger than 1.0, on the other hand, ions of the element of the Group IV becomes excessive relative to the phosphoric diester polymerizable monomer whereby the hydrogenphosphate diester groups that ionically bond to the ions of the element of the Group IV becomes in short supply. As a result, the crosslinking density decreases and the adhesive property is not exhibited to a sufficient degree.

Upon containing ions of the element of the Group IV in a specified amount according to the present invention, a particularly large adhering strength is obtained as compared to when other polyvalent metal ions are made present probably because of the reasons mentioned below though they are not clear yet. That is, if ions of the element of the Group IV are made present in a system that contains the phosphoric diester polymerizable monomer, a firm ionic bond is formed by the acid group in the polymerizable monomer and by the ion of the element of the Group IV. When the composition having the ionic bond is polymerized and cured, it is considered that the adhering force is produced by the polymerization and, besides, the adhering force due to the ionic crosslinking of a polymer chain formed by the polymerization of the ionic bond synergistically works to further increase the adhering strength.

With the polyvalent metal ions such as aluminum ions and calcium ions added to the conventional dental adhesive compositions, the ionic bond can be formed by up to three molecules of the polymerizable monomer that has an acid group. With the ions of the element of the Group IV, however, at least four or more molecules of the polymerizable monomer that has an acid group can form the ionic bond. Therefore, use of ions of the element of the Group IV makes it possible to further increase the crosslinking density than when other polyvalent metal ions are used presumably enabling the adhering strength and the durability of adhesion to be improved. According to the present invention, further, the polymerizable monomer having an acid group is a phosphoric diester polymerizable monomer as described above, and in which the hydrogenphosphate diester group in the monomer has a high acidity and more easily ionically bonds to the ion of the element of the Group IV than the other acid groups. It is, therefore, presumed that the crosslinking density increases more effectively realizing a large adhering strength.

The kind and content of ions of the element of the Group IV in the dental adhesive composition can be found by using an inductively coupled plasma (ICP) emission analyzer or a fluorescent X-ray (XRF) analyzer after the solid components have been removed. Concretely speaking, when the ICP emission analyzer is used, the adhesive composition is diluted with a water-soluble organic solvent down to a concentration of 1 mass %, and the obtained diluted solution is filtered by using a syringe filter or the like filter to remove solid components. The ionic species and concentration of the obtained filtrate are measured by using the ICP emission analyzer to calculate the species and amount of ions the element of the Group IV in the adhesive composition. When the XRF analyzer is used, on the other hand, the adhesive composition is filtered by using the syringe filter or the like filter to remove solid components. The ionic species and concentration of the obtained filtrate are measured by using the XRF analyzer to calculate the species and amount of ions of the element of the Group IV in the adhesive composition. Metal ionic species other than the ionic species of the element of the Group IV and the contents thereof can also be measured by the same method.

Similarly, to measure the kind and content of the phosphoric diester polymerizable monomer in the dental adhesive composition, the phosphoric acid type polymerizable monomers {hereinafter, polymerizable monomers pertaining to both (A-1) the phosphoric diester polymerizable monomer and (A-2) the phosphoric acid group-containing polymerizable monomer} are isolated from the composition by using a high-speed liquid chromatography for isolation, the molecular weight is found by analyzing the mass of the isolated phosphoric acid type polymerizable monomer and, further, the structure thereof is determined by measuring the nuclear magnetic resonance spectrum (NMR). Upon measuring the NMR of $^{31}P$, in particular, a hydrogenphosphate diester group can be identified from a chemical shift value thereof. The chemical shift value can be determined by measuring $^{31}P$-NMR of a known compound under the same conditions (diluting solvent, concentration, temperature) and using it as a standard. As the known compound having the hydrogenphosphate diester group, a hydrogenphosphate dimethyl ester is used. Further, the content of the phosphoric diester polymerizable monomer can be measured through a high-speed liquid chromatography by using the polymerizable monomer isolated by using the high-speed liquid chromatography for isolation, preparing a calibration curve from the above standard substance, and adding an internal standard substance to part of the above filtrate.

In the dental adhesive composition of the present invention, there is no particular limitation on the method of containing ions of the element of the Group IV in the system. Namely, in preparing the dental adhesive composition, a substance that serves as a source of ions of the element of the Group IV is added or contacted to the polymerizable monomer component that contains the phosphoric diester polymerizable monomer so that ions of the element of the Group IV are eluted out in the system in the above-mentioned amount.

As a compound that serves as a source of ions of the element of the Group IV, there can be exemplified a simple element of the Group IV, a polyvalent metal ion-eluting filler containing ions for eluting ions of the element of the Group IV and a compound of the element of the Group IV. As the compound of the element of the Group IV, there can be exemplified a metal salt of the element of the Group IV, a metal halide of the element of the Group IV and a metal alkoxide of the element of the Group IV ($B_{alk}$). As the metal salt, there can be exemplified enolate of 1,3-diketone, citrate, tartarate, fluoride, malonate, glycolate, lactate, phthalate, isophthalate, terephthalate, acetate and methoxyacetate. As the metal halide, there can be exemplified titanium fluoride, zirconium fluoride and hafnium fluoride. As the metal alkoxide of the element of the Group IV ($B_{alk}$), there can be exemplified titanium methoxide, titanium ethoxide, titanium propoxide, titanium isopropoxide, zirconium methoxide, zirconium ethoxide, zirconium propoxide, and zirconium isopropoxide. Among them, titanium methoxide, titanium ethoxide, titanium propoxide and titanium isopropoxide are particularly preferred. Among those compounds, the lower metal alkoxide of the element of the Group IV having not more than 4 carbon atoms is more preferred from such a standpoint that metal ions can be quickly eluted out, that the by-product is an alcohol which can be easily removed without affecting the adhering strength and that the handling is easy. Here, some compounds of the element of the Group IV dissolve very slowly. It is, therefore, recommended to make sure their usability by conducting experiments in advance.

Simple titanium or zirconium and oxides thereof for use as compounds of sources of ions of the element of the Group IV are in many cases insoluble in the polymerizable monomer or in the organic solvent and, usually, do not almost elute out corresponding metal ions even in the presence of water, and cannot, therefore, be used as sources of ions of the element of the Group IV. Further, the polyvalent metal ion-eluting filler containing ions of the element of the Group IV, too, does not almost elute out ions of the element of the Group IV even in the presence of water, and cannot be used as a source of ions of the element of the Group IV. In general, further, a salt of a strong acid tends to difficulty exchange salt with a weak acid. Therefore, an acid having a pKa value smaller than a pKa value based on the first dissociation of phosphoric acid, i.e., a metal salt of an acid stronger than the phosphoric acid is not suited for use as a source of ions of the element of the Group IV because of insufficient ionic bond of the free ion of the element of the Group IV and the hydrogenphosphate diester group.

It is desired that the dental adhesive composition of the present invention is produced by using the metal alkoxide of the element of the Group IV ($B_{alk}$) as a source of ions of the element of the Group IV from the standpoint of easy production. Namely, the dental adhesive composition is produced by mixing a polymerizable monomer containing at least 10 mass % of phosphoric diester polymerizable monomer and a metal alkoxide of an element of the Group IV in such an amount that the content of ions of the element of the Group IV is 0.1 to 1.0 in terms of a mole ratio to the hydrogenphosphate diester groups of the phosphoric diester polymerizable monomer. When the dental adhesive composition of the invention is to be blended with water as will be described later, the phosphoric diester polymerizable monomer and the metal alkoxide of the element of the Group IV are mixed first and are, thereafter, mixed to water. When a polymerizable monomer other than the phosphoric diester polymerizable monomer is to be mixed, the other polymerizable monomer is mixed with the phosphoric acid diester polymerizable monomer, first, mixed to the metal alkoxide of the element of the Group IV and is, thereafter, mixed to water. Or, the phosphoric diester polymerizable monomer is mixed to the metal alkoxide of the element of the Group IV and is, thereafter mixed to water and, finally, the other polymerizable monomer is mixed thereto.

The phosphoric diester polymerizable monomer and the compound of the element of the Group IV must be mixed together in the absence of water. If they are mixed together in the presence of water, ions of the element of the Group IV precipitate as solid oxide making it difficult to form ionic bond with the hydrogenphosphate diester group. That is, if the phosphoric diester polymerizable monomer and the compound of the element of the Group IV are mixed together in the presence of water, adhering strength is not obtained as desired even immediately after the preparation of the composition. Therefore, when water is to be added to the dental adhesive composition, it is necessary that water is added after having mixed the polymerizable monomer that contains at least 10 mass % of the phosphoric diester polymerizable monomer and the compound of the element of the Group IV and after the ionic bond is formed between them to a sufficient degree.

(E) Water.

Even when no water is contained, the dental adhesive composition of the present invention is capable of exhibiting a demineralization action to a degree effective for increasing the adhering force provided it has acidity owing to the presence of water in the breathing in the oral cavity or water present on the teeth surfaces. However, when the dental adhesive composition of the present invention is used as a primer or a dental adhesive material of the one-step type that does not use primer, it is desired to add water (E) from the standpoint of accelerating the demineralization and obtaining a larger adhering strength. When water is to be added as described above, the phosphoric diester polymerizable monomer and the compound of the element of the Group IV must be mixed together first. To effect the demineralization with acid to a sufficient degree, it is desired that water is added in an amount of 3 to 150 parts by mass and, more preferably, 5 to 100 parts by mass per 100 parts by mass of the polymerizable monomer component.

(M) Other Metal Ions.

The dental adhesive composition of the present invention may contain other metal ions (M) in addition to the ions of the element of the Group IV (B). As the other metal ions, there can be exemplified monovalent and divalent metal ions, such as alkali metal ions and alkaline earth metal ions, as well as trivalent metal ions such as of aluminum (III), iron (III), ruthenium (III), cobalt (III) and lanthanum (III). From the standpoint of favorably developing ionic crosslinking by the ions of the element of the Group IV, it is desired that the ratio of the total ionic valency of all of these other metal ions is not larger than 0.5 and, more preferably, not larger than 0.3 to the total ionic valency of all metal ions that are contained. The total ionic valency is the sum of mol numbers of each of ion species multiplied by the valencies.

If the dental adhesive composition of the invention contains other metal ions in large amounts dissolved therein, the hydrogenphosphate diester groups possessed by the phosphoric diester polymerizable monomer are neutralized by being ionically bonded with the metal ions. Therefore, if the ratio of "the total ionic valency of metal ions"/"the total valency of hydrogenphosphate diester groups possessed by phosphoric diester polymerizable monomer" becomes not smaller than 1.0, then the composition, usually, does not exhibit acidity. The dental adhesive composition of the invention produces a large adhering strength even if it no longer exhibits acidity. However, the dental adhesive composition still exhibiting acidity is capable of imparting an etching function (function for demineralization teeth) and producing a large adhering strength, which is desirable. In order for the dental adhesive composition of the present invention to express an etching function, therefore, the amount of the metal ions dissolved therein must be so adjusted that the composition becomes acidic. Or, when the ratio of "the total ionic valency of metal ions"/"the total valency of hydrogenphosphate diester groups possessed by phosphoric diester polymerizable monomer" becomes not smaller than 1.0, other acidic substances must be contained to maintain the acidity.

The dental adhesive composition of the present invention should have an acidity, i.e., should have a pH value which is less than 4.8 as measured by a method described below. That is, the adhesive composition is mixed to an ethanol so that the concentration thereof is 10 mass %, and the pH of the mixed solution is quickly measured to learn the acidity. Though the pH can be measured by a known method, it is simple and desired to use a method which takes a measurement by using a pH meter that uses a pH electrode calibrated by using a neutral phosphate pH standard solution (pH 6.86) and a phthalate pH standard solution (pH 4.01). There is no problem if ethanol used for the dilution has a purity of not lower than 99.5% and if a pH value of the ethanol alone is 4.8 to 5.0 as measured by a method described below. From the standpoint of the tooth-demineralization intensity, it is desired that the dental adhesive composition has a pH in a range of 0.5 to 4.0 and, more desirably, 1.0 to 3.0 as measured by the above method.

As other acidic substances to be separately added, there are used those having pKa values of not smaller than 2.15 in water at 25° C. From the standpoint of the intensity of the tooth-demineralization function, however, it is desired to use those having pKa values of not larger than 6.0 and, more desirably, not larger than 4.0. Examples that can be favorably used include citric acid, tartaric acid, hydrogen fluoride, malonic acid, glycolic acid, lactic acid, phthalic acid, isophthalic acid, terephthalic acid and methoxyacetic acid. As other acidic substances, further, there can be used a polymerizable monomer having an acid group other than the acid group derived from the phosphoric acid, such as 2-(6-methacryloxyhexyl)malonic acid, 2-(10-methacryloxydecyl)malonic acid, trimellitic acid-4-(2-methacryloxyethyl)ester, N-methacryloylglutamic acid, 1,2,4,5-benzenetetracarboxylic acid-2,4-bis(2-methacryloxyethyl)ester, and 3,3,4,4-biphenyltetracarboxylic acid-4,4-bis(2-methacryloxyethyl)ester.

Even when other acidic substances are to be contained according to the present invention, attention must be given not to use, as the acidic substances, strong acids having pKa values smaller than a pKa value (2.15) which is based on the first dissociation of the phosphoric acid in water at 25° C. This is because the conjugated base ions of such strong acids contained in the dental adhesive composition result in a decrease in the strength of adhesion. The reason is because the conjugated base ion of the strong acid undergoes the competitive ionic reaction with the acid group of the phosphoric diester polymerizable monomer. Namely, the conjugated base ions of the strong acid hinder the formation of ionic bond between the acid group of the phosphoric diester polymerizable monomer and the ion of the element of the Group IV. Therefore, the conjugated base ions of the strong acid must not be substantially contained, though they may be contained to some extent that will not affect the effect. If contained, it is desired that the content thereof is not larger than 5 mol % and, more desirably, not larger than 3 mol % relative to the ions of the element of the Group IV.

When other acidic substances are to be contained, it becomes necessary to set the ratio of "the total valency of the acidic substances except for phosphoric diester polymerizable monomer"/"the total ionic valency of the ions of the Group IV elements" to be smaller than 1.0. If the ratio is not smaller than 1.0, the adhering strength decreases. This is because the phosphoric diester polymerizable monomer and other acidic substances form ionic bond competitively with ions of the element of the Group IV. Therefore, if the ratio exceeds 1.0, formation of ionic bond between the phosphoric diester polymerizable monomer and the ion of the element of the Group IV is greatly suppressed. More preferably, the ratio should be smaller than 0.5.

If the dental adhesive composition of the invention contains conjugated base ions of acids other than the phosphoric diester polymerizable monomer, can be confirmed by the measurement using the ion chromatography. Concretely speaking, the adhesive composition is extracted with water, the obtained aqueous phase is filtered, and the filtrate is measured by using the ion chromatography.

(D) Fluoride Ions.

When water is contained, the dental adhesive composition of the invention provides a large adhering strength if it is produced by the above-mentioned particular method accompanied, however, by a probability in that the solid oxide of ions of the element of the Group IV precipitates while being stored for extended periods of time resulting in a decrease in the amount of ions of the element of the Group IV in the composition, in a decrease in the adhering strength and causing the nozzle of the container to be clogged. Even when no water is contained, the dental adhesive composition may absorb water in the air as the container is opened and closed repetitively and the solid matter may precipitate. In such a case, if the composition contains fluoride ions ($F^-$) (D), it is allowed to prevent the precipitation of solid oxide caused by water and to improve the storage stability of the composition. Though the reason is not clear why the precipitation of oxide of ions of the element of the Group IV can be prevented by the presence of the fluoride ions ($F^-$), it is presumed that the ionically crosslinked body of the phosphoric diester polymerizable monomer and the ion of the element of the Group IV is partly fluorinated by the fluoride ions, and the fluorinated ionically crosslinked body is little subject to be hydrolyzed.

Upon adding the fluoride described below to the dental adhesive composition of the invention, the fluoride ions can be released in the composition. There can be used any fluoride as a source of fluoride ions without limitation provided it is capable of releasing fluoride ions. Concretely, there can be used hydrofluoric acid, metal fluoride, ammonium fluorides and fluoroaluminosilicate glass. Among them, the metal fluoride is particularly preferred. Preferred examples of the metal fluoride include alkali metal fluorides such as sodium fluoride, potassium fluoride and lithium fluoride; alkaline earth metal fluorides such as calcium fluoride and magnesium fluoride; earth metal fluorides such as aluminum fluoride, yttrium fluoride, lanthanum fluoride and ytterbium fluoride; fluorides of metals of the Group IV such as titanium fluoride and zirconium fluoride; and zinc fluoride. Among them, the alkali metal fluoride and fluorides of the elements of the Group IV are preferred, and the alkali metal fluoride is more preferred. The sodium fluoride is most preferred.

The fluoride ions may be added being adjusted in suitable amounts so as to prevent the precipitation of the oxide of the metal of the Group IV. If the amount thereof is too small, the effect of addition is not obtained. As described above, on the other hand, the fluoride ions are conjugated base ions of the hydrofluoric acid that exhibits a pKa value larger than the pKa value (2.15) based on the first dissociation of the phosphoric acid. It is, therefore, desired that the mole ratio of the fluoride ions is smaller than 1.0 relative to the "total ionic valency of ions of the element of the Group IV". Further, when there is added a compound such as an alkali metal fluoride which is a source of fluoride ions, that could become a source of metal ions other than the ions of the element of the Group IV, it is desired that the compound is added in such an amount that the mol ratio of the total ionic valency of ions of other metals becomes not larger than 0.5 and, more preferably, not larger than 0.3 to the total ionic valency of the whole metal ions. A preferred amount of the fluoride ions is, in terms of mole ratio, 0.4 to 4.0 and, more desirably, 0.4 to 1.7 to the ions of the element of the Group IV.

When a fluoride of the element of the Group IV is used as the fluoride, the fluoride may be mixed to the phosphoric diester polymerizable monomer in the absence of water like in the above-mentioned method of adding the metal alkoxide of the element of the Group IV. When other fluorides are to be added, there is no particular limitation on the method of addition. When the alkali metal fluoride is used, in particular, the alkali metal fluoride may be mixed to the phosphoric diester polymerizable monomer together with the metal alkoxide of the element of the Group IV in the absence of water. Or, an aqueous solution of the alkali metal fluoride may be added after the phosphoric diester polymerizable monomer and the metal alkoxide of the element of the Group IV have been mixed together.

The fluoride ions in the dental adhesive composition are such that so far as the composition is homogeneous, the fluoride that is added is almost all ionized and is present in the composition. When released out from the fluoroaluminosilicate glass, however, the content of the fluoride ions can be found by the measurement using an anion chromatography. If concretely described, the fluoride ions are diluted in a pure form down to 1%, and the diluted solution is filtered by using a syringe filter to remove solid components. The concentration of fluoride ions contained in the filtrate is measured by using the anion chromatography, and the content of fluoride ions in the dental adhesive composition is calculated.

The dental adhesive composition of the invention is used for adhering tooth in the dental use. In particular, the dental adhesive composition is useful as a dental adhesive material for adhering a dental restorative such as composite resin or prosthetic or for adhering an instrument for correction of irregularities of teeth such as bracket to the teeth, and as a primer applied for treating the tooth surfaces prior to applying the adhesive material to the tooth surface. Usually, the primer applied to the to-be-applied body such as the tooth surface is not cured by itself but is cured together with the adhesive material that is further applied onto the primer that is applied. The composition of the present invention is preferably used as an adhesive material, particularly, for a composite resin and is, further, preferably used as a one-step type adhesive material that also has a primer function. When the composition of the invention is used as a primer for adhering the composite resin, on the other hand, the composite resin may be filled and adhered without using the adhesive material. That is, the composite resin is directly filled in the tooth surface onto where the primer is applied. The composite resin that is filled is then optically cured so that the primer is also cured, and is thus adhered to the tooth. When used in a manner as described above, there is no need of applying the adhesive material or of effecting the curing by polymerization, and the clinical operation becomes easy, which is desirable.

(C) Polymerization Initiators.

The dental adhesive composition of the present invention may be blended with an effective amount of a polymerization initiator. The polymerization initiator is necessary particularly when the composition is used as the dental adhesive. As the polymerization initiator, it is desired to use a photopolymerization initiator since it can be polymerized and cured at any timing. As the photopolymerization initiator, there can be preferably used α-diketones such as camphorquinone, benzyl, α-naphthyl, acetonaphthone, naphthoquinone, 1,4-phenanthrenequinone, 3,4-phenanthrenequinone and 9,10-phenanthrenequinone; thioxanthones such as 2,4-diethylthioxanthone; α-aminoacetophenones such as 2-benzyl-dimethylamino-1-(4-morpholinophenyl)-butanone-1, 2-benzyl-diethylamino-1-(4-morpholinophenyl)-butanone-1, 2-benzyl-dimethylamino-1-(4-morpholinophenyl)-propanone-1, 2-benzyl-diethylamino-1-(4-morpholinophenyl)-propanone-1, 2-benzyl-dimethylamino-1-(4-morpholinophenyl)-pentanone-1 and 2-benzyl-diethylamino-2-(4-morpholinophenyl)-pentanone; and acylphosphinoxide derivatives such as 2,4,6-trimethylbenzoyldiphenylphosphinoxide and bis(2,6-dimethoxybenzoyl)-2,4,4-trimethylpentylphosphinoxide. As required, further, there can be used chemical polymerization initiators such as borate compounds comprising butyltriphenylboric acid, tetraphenylboric acid, sodium salt of tetrakis(p-tolyl) boric acid or triethanolammonium salt; diacyl peroxides such as dibenzoyl peroxide and di(4-methylbenzoyl) peroxide; alkyl hydroperoxides such as t-butyl hydroperoxide and 1,1,3,3-tetramethylbutyl hydroperoxide; and barbituric acids. In order to enhance the polymerization initiating activity of the hydroperoxides and/or the borates, further, there can be simultaneously used transition metal compounds such as vanadium compound, chromium compound, manganese compound, iron compound and cobalt compound. Desirably, there can be used the vanadium compound such as oxovanadium (IV) bis(maltolato) and divanadium pentoxide. Further, when the composition of the invention is used as a primer for the composite resin and is directly adhered to the tooth surface without using adhesive material, the primer is blended with the vanadium compound while the composite resin is blended with hydroperoxides in addition to being blended with the photopolymerization initiator to obtain a large adhering strength.

As the polymerization accelerator that can be used in combination with the polymerization initiator, there can be exemplified tertiary amines such as N,N-dimethylaniline, N,N-diethylaniline, N,N-di-n-butylaniline, N,N-dibenzylaniline, N,N-dimethyl-p-toluidine, N,N-diethyl-p-toluidine, N,N-dimethyl-m-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amyl ester, N,N-dimethylanthranic acid methyl ester, N,N-dihydroxyethylaniline, N,N-dihydroxyethyl-p-toluidine, p-dimethylaminophenetyl alcohol, p-dimethylaminostylbene, N,N-dimethyl-3,5-xylydine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylsteallylamine, N,N-dimethylaminoethylacrylate, N,N-dimethylaminoethylmethacrylate and 2,2'-(n-butylimino) diethanol; barbituric acids such as 5-butylbarbituric acid and 1-benzyl-5-phenylbarbituric acid; and mercapto compounds such as dodecylmercaptane and pentaerythritol tetrakis (thioglycolate).

The polymerization initiator is added in an amount of 0.01 to 10 parts by mass and, preferably, 0.1 to 5 parts by mass per 100 parts by mass of the whole polymerizable monomer components. To further enhance the polymerization initiating activity, there may be added electron acceptors such as iodonium salt, trihalomethyl-substituted S-triazine and phenancylsulfonium salt compound in addition to the above polymerization initiators and polymerization accelerators.

Further, a filler may be added to the dental adhesive composition of the invention. As the filler, there can be preferably exemplified silica and inorganic fillers such as zirconia, titania, silica-zirconia and silica-titania. These inorganic fillers can be improved for their affinity to the polymerizable monomer by being treated to be hydrophobic with a surface-treating agent as represented by a silane coupling agent in order to improve the mechanical strength and water-resisting property. The hydrophobic property can be imparted by a known method. As the silane coupling agent, there can be preferably used methyltrimethoxysilane, methyltriethoxysilane, methyltrichlorosilane, dimethyldichlorosilane, trimethylchlorosilane, vinyltrimethoxysilane, vinyltriethoxysilane, vinyltrichlorosilane, vinyltriacetoxysilane, vinyltris(β-methoxyethoxy) silane, γ-methacryloyloxypropyltrimethoxysilane, γ-methacryloxypropyltris(β-methoxyethoxy) silane, γ-chloropropyltrimethoxysilane, γ-glycidoxypropyltrimethoxysilane, γ-glycidoxypropylmethyldiethoxysilane, β-(3,4-epoxycyclohexyl)ethyltrimethoxysilane, N-phenyl-γ-aminopropyltrimethoxysilane and hexamethyldisilazane. The inorganic filler is added, usually, in an amount in a range of 2 to 400 parts by mass and, more preferably, 5 to 100 parts by mass per 100 parts by mass of the polymerizable monomer components. When the dental adhesive composition of the invention is used as an adhesive for composite resin or as a primer, in particular, the inorganic filler is used in an amount in a range of 2 to 60 parts by mass and, more preferably, 5 to 40 parts by mass.

The dental adhesive composition of the invention may be further blended with a volatile organic solvent. The volatile organic solvent that can be desirably used is the one that is volatile at room temperature and is soluble in water. Volatile referred to here has a meaning in that a boiling point under 760 mmHg is not higher than 100° C. and a vapor pressure at 20° C. is not less than 1.0 kPa. Further, soluble in water refers to that the solubility in water at 20° C. is not less than 20 g/100 ml and, preferably, is compatible with water at any ratio at 20° C. As the volatile water-soluble organic solvent, there can be exemplified methanol, ethanol, n-propanol, isopropyl alcohol, tartiarybutanol, acetone and methyl ethyl ketone. As required, a plurality of these organic solvents can be used being mixed together. By taking toxicity to the living body into consideration, it is desired to use ethanol, isopropyl alcohol and acetone. The volatile organic solvents are, usually, added in amounts in a range of 2 to 400 parts by mass and, more preferably, 5 to 100 parts by mass per 100 parts by mass of the whole polymerizable monomer components. Like the water described above, when the dental adhesive composition of the invention is applied onto the tooth surface as the primer or as the adhesive material, the volatile organic solvents, too, are removed by blowing the air prior to curing the adhesive composition.

As required and irrespective of the use, furthermore, an organic viscosity-imparting material comprising a high molecular compound such as polyvinyl pyrrolidone, carboxymethyl cellulose or polyvinyl alcohol can be added to the adhesive composition of the invention in a range in which they do not lower the properties thereof. Moreover, a variety of additives such as ultraviolet ray absorber, dye, antistatic agent, pigment and perfume may be selectively added as required.

EXAMPLES

The present invention will now be concretely described by way of Examples and Comparative Examples which, however, are not to limit the invention. Further, it does not mean that the combinations of features described in Examples are all essential for solving the problems of the invention. Abbreviated names and abbreviated signs appearing in Examples are as described below.

Abbreviated Names and Abbreviated Signs:
[(A) Polymerizable monomers]
(A-1) Phosphoric diester polymerizable monomers.
PM2: bis(2-methacryloyloxyethyl)hydrogenphosphate
Phenyl-P: 2-methacryloyloxyethylphenyl hydrogenphosphate
(A-2) Phosphoric acid group-containing polymerizable monomer.
PM-1: 2-methacryloyloxyethyl dihydrogenphosphate
(A-3) Non-acid group-containing polymerizable monomers.
BisGMA: 2,2'-bis(4-(2-hydroxy-3-methacryloxypropoxy)phenyl)propane
3G: triethylene glycol dimethacrylate
HEMA: 2-hydroxyethyl methacrylate
14G: polyethylene glycol (average polymerization degree, 14) dimethacrylate
[(B) Ions of elements of the Group IV]
($B_{alk}$) Metal alkoxides of elements of the Group IV
Ti(O-i-Pr)$_4$: titanium tetraisopropoxide
Zr(O-i-Pr)$_4$: zirconium tetraisopropoxide
(Other Compounds of elements of the Group IV)
ZrO$_2$: zirconium oxide
TiF$_4$: titanium fluoride
[(C) Polymerization initiators]
(Photopolymerization initiators)
CQ: camphorquinone
DMBE: ethyl p-N,N-dimethylaminobenzoate
(Other polymerization initiators)
Perocta H: 1,1,3,3-tetramethylbutylhydroperoxide
BMOV: oxovanadium(IV) bis(maltolato)
[(D) Fluoride ions]
(Metal fluoride)
NaF: sodium fluoride
[(M) Other metal ions]
(Other compounds of metal ion sources)
Al(O-i-Pr)$_3$: aluminum triisopropoxide
Ca(O-i-Pr)$_2$: calcium diisopropoxide
Ce(O-i-Pr)$_4$: cerium tetraisopropoxide
La(O-i-Pr)$_3$: lanthanum triisopropoxide
Sc(O-i-Pr)$_3$: scandium triisopropoxide
TiO$_2$: titanium oxide
Y(O-i-Pr)$_3$: yttrium triisopropoxide
Yb(O-i-Pr)$_3$: ytterbium triisopropoxide
[Other components]
(Volatile water-soluble organic solvents)
IPA: isopropyl alcohol
acetone
(Polymerization prohibitors)
BHT: 2,6-di-t-butyl-p-cresole
HQME: hydroquinonemonomethyl ether
(Ultraviolet ray absorber)
BS110: 2-hydroxy-4-methoxybenzophenone
(Inorganic fillers)
F1: A mixture of a spherical silica-zirconia (average particle diameter of 0.4 μm) treated to be hydrophobic with a γ-methacryloyloxypropyltrimethoxysilane and a spherical silica-zirconia (average particle diameter of 0.07 μm) treated to be hydrophobic with the γ-methacryloyloxypropyltrimethoxysilane at a mass ratio of 70:30.
F2: Fumed silica (average particle diameter of 0.007 μm) of which the surfaces are treated with the dimethyldichlorosilane.
MF: A fluoroaluminosilicate glass powder (Tokuso Ionomer manufactured by Tokuyama Co.) pulverized down to an average particle diameter of 0.4 μm by using a wet continuous-type ball mill (SC Mill manufactured by Mitsui Kozan Co.).

In Examples and Comparative Examples described below, various measurements were taken by the following methods.
(1) Method of Measuring Metal Ions.

The dental adhesive composition of the invention was prepared, stirred and was filtered by using a syringe filter. The filtrate was subjected to the fluorescent X-ray (XRF) analysis to measure the concentrations of metal ions (mmols/g) contained in a gram of the polymerizable monomer.
(2) Method of Measuring Phosphoric Acid Type Polymerizable Monomer.

The dental adhesive composition of the invention was prepared, stirred, and 0.2 g of which was weighed and put into a 100-ml sample tube and was diluted to 1 mass % with IPA.

The solution was filtered by using the syringe filter, and the filtrate was measured with HPLC to measure the concentration of the phosphoric acid type polymerizable monomer (mmols/g) contained in a gram of the polymerizable monomer.

(3) Method of Measuring Fluoride Ions.

2 Grams of the dental adhesive composition, 100 g of water and 10 g of diethyl ether were vigorously mixed together. After left to stand still, the aqueous phase was filtered by using the syringe filter, and the filtrate was measured by using the ion chromatography to measure the concentration of fluoride ions (mmols/g) contained in a gram of the polymerizable monomer.

(4) Method of Measuring pH of the Dental Adhesive Composition.

2 Grams of the dental adhesive composition and 8 g of anhydrous ethanol were mixed together, and a pH thereof was quickly measured by using a pH electrode (GTS-5211C manufactured by Toa DKK Co.) that has been calibrated by using a neutral phosphate pH standard solution (pH 6.86) and a phthalate pH standard solution (pH 4.01).

(5) Method of Preparing Test Pieces.

a) Method of preparing an adhesion test piece I (applied when the dental adhesive composition is used as a dental adhesive material).

Within 24 hours after the slaughter, a bovine foretooth was pulled out, and the enamel surface and the dentin surface were ground by using a #600 emery paper while pouring water so as to be in parallel with the labial face. Next, the compressed air was blown onto the surfaces for about 10 seconds to dry. Thereafter, a double-sided adhesive tape having a hole of 3 mm in diameter perforated therein was fixed to either the enamel surface or the dentin surface and, thereafter, a paraffin wax of a thickness of 0.5 mm having a hole of 8 mm in diameter perforated therein was fixed to the hole in concentric therewith to form a mimic cavity. The dental adhesive material was applied into the mimic cavity, left to stand for 20 seconds and, thereafter, the compressed air was blown thereto for about 10 seconds to dry followed by the irradiation with light from a dental visible ray irradiator (Tokuso Power-Light manufactured by Tokuyama Co.) for 10 seconds. Further, a dental composite resin (Estelite Σ manufactured by Tokuyama Dental Co.) was applied thereon, and was irradiated with light by using the above visible ray irradiator for 30 seconds to prepare an adhesion test piece I.

b) Method of preparing an adhesion test piece II (applied when the dental adhesive composition is used as a primer).

The dental primer was applied into the mimic cavity formed by the same method as the above method a) of preparing the adhesion test piece I, left stand for 20 seconds and, thereafter, the compressed air was blown thereto for about 10 seconds to dry. Thereafter, a two-step type adhesive material for composite resin (bonding material of Tokuso Macbond II manufactured by Tokuyama Co.) was applied thereon and was irradiated with light from the dental visible ray irradiator (Tokuso Power-Light manufactured by Tokuyama Co.) for 10 seconds. Further, a dental composite resin (Estelite Σ manufactured by Tokuyama Dental Co.) was applied thereon, and was irradiated with light by using the above visible ray irradiator for 30 seconds to prepare an adhesion test piece II.

c) Method of preparing an adhesion test piece III (applied when the dental adhesive composition is used as a dental adhesive that uses a dental primer).

The dental primer of the two-step type adhesive material for composite resin (Tokuso Macbond II) was applied into the mimic cavity formed by the same method as the above method a) of preparing the adhesion test piece I, left stand for 20 seconds and, thereafter, the compressed air was blown thereto for about 10 seconds to dry. Thereafter, the dental adhesive material was applied thereon and was irradiated with light from the dental visible ray irradiator (Tokuso Power-Light manufactured by Tokuyama Co.) for 10 seconds. Further, a dental composite resin (Estelite Σ manufactured by Tokuyama Dental Co.) was applied thereon, and was irradiated with light by using the above visible ray irradiator for 30 seconds to prepare an adhesion test piece III.

d) Method of preparing an adhesion test piece VI (applied when the dental adhesive composition is used as a dental primer for composite resin).

The dental primer was applied into the mimic cavity formed by the same method as the above method a) of preparing the adhesion test piece I, left stand for 20 seconds and, thereafter, the compressed air was blown thereto for about 10 seconds to dry. Thereafter, a separately prepared composite resin was applied thereon and was irradiated with light from the visible ray irradiator for 20 seconds to prepare an adhesion test piece VI.

(6) Method of Testing Durability of Adhesion.

Any one of the adhesion test piece I, II, III or IV was put into a thermal shock tester, dipped in a water vessel maintained at 4° C. for one minute, transferred into a water vessel maintained at 60° C. and was dipped therein for one minute, and was returned again into the water vessel maintained at 4° C. The above operation was repeated 3000 times. Thereafter, by using a tension tester (Autograph manufactured by Shimazu Seisakusho Co.), the adhesion test piece was pulled at a crosshead speed of 2 mm/min to measure the tensile strength of adhesion between the enamel or the dentin and the composite resin. Four test pieces were measured for their tensile strength of adhesion by the above method for each test, and average valves thereof were measured as adhering strengths after the durability test to evaluate the durability of adhesion.

(7) White Precipitation after Storage.

Grams of the dental adhesive composition containing ion of an element of the Group IV was put into a 10-ml screw tube and was stored in an incubator maintained at 25° C. for 90 days. Thereafter, the screw tube was vigorously shaken, and the adhesive composition was regarded to be X when it was clouded as compared to before being stored and ○ when it was not clouded.

Example 1

25.0 Grams of an equimolar mixture of PM1 and PM2, 30 g of BisGMA, 20 g of 3G and 25 g of HEMA as polymerizable monomers; 4.4 g of titanium isopropoxide as a source of titanium ions; 1.25 g of camphorquinone, 1.25 g of DMBE and 85 g of IPA as polymerization initiators; and 0.25 g of BHT, 0.19 g of HQME and 9.8 g of hydrophobic fumed silica having an average particle diameter of 0.01 μm as other components, were mixed and stirred together until it became homogeneous. Thereafter, 19 g of distilled water was added thereto, and the mixture was mixed and stirred again until it became homogeneous to thereby obtain a one-step type adhesive material comprising the dental adhesive composition of the invention for composite resin.

The adhesive material was measured for its phosphoric acid type polymerizable monomer, metal ions and pH. By using the adhesive material, an adhesion test piece was prepared according to the method of preparing the adhesion test piece I and was tested for its durability of adhesion to the enamel and to the dentin. The composition of the adhesive material was as shown in Table 1 and the evaluated results were as shown in Table 2.

Examples 2 to 10

Adhesive materials of different compositions shown in Table 1 were prepared in accordance with the method of Example 1. The obtained one-step type adhesive materials for composite resin were measured for their phosphoric acid type polymerizable monomers, metal ions and pHs. By using these adhesive materials, adhesion test pieces were prepared according to the method of preparing the adhesion test piece I and were tested for their durability of adhesion to the enamel and to the dentin. The compositions of the adhesive materials were as shown in Table 1 and the results were as shown in Table 2.

Comparative Examples 1 to 17

Adhesive materials of different compositions were prepared in accordance with the method of Example 1. The obtained one-step type adhesive materials for composite resin were measured for their phosphoric acid type polymerizable monomers, metal ions and pHs. By using these adhesive materials, adhesion test pieces were prepared according to the method of preparing the adhesion test piece I and were tested for their durability of adhesion to the enamel and to the dentin. The compositions of the adhesive materials were as shown in Table 3 and the results were as shown in Table 4.

TABLE 1

| Ex. No. | Adhesive for composite resin (parts by mass)[Note 1] Polymerizable monomer | |
|---|---|---|
| | Phosphoric diester polymerizable monomer | Other polymerizable monomers |
| 1 | PM2 (15.1) | PM1 (9.9), BisGMA (30), 3G (20), HEMA (25) |
| 2 | PM2 (15.1) | PM1 (9.9), BisGMA (30), 3G (20), HEMA (25) |
| 3 | PM2 (15.1) | PM1 (9.9), BisGMA (30), 3G (20), HEMA (25) |
| 4 | PM2 (15.1) | PM1 (9.9), BisGMA (30), 3G (20), HEMA (25) |
| 5 | PM2 (15) | PM1 (9.9), BisGMA (30), 3G (20), HEMA (25) |
| 6 | PM2 (15.1) | PM1 (9.9), BisGMA (30), 3G (20), HEMA (25) |
| 7 | PM2 (15.1) | PM1 (9.9), BisGMA (30), 3G (20), HEMA (25) |
| 8 | PM2 (15.1) | PM1 (9.9), BisGMA (30), 3G (20), HEMA (25) |
| 9 | phenyl-P (25.0) | BisGMA (30), 3G (20), HEMA (25) |
| 10 | PM2 (25.0) | BisGMA (30), 3G (20), HEMA (25) |

| Ex. No. | Adhesive for composite resin (parts by mass)[Note 1] | | | | |
|---|---|---|---|---|---|
| | Compounds of Group IV element ion sources | Compounds of other metal ion sources | Organic solvent | Water | Polymerization initiator |
| 1 | Ti(O—i-Pr)$_4$ (6.8) | — | IPA (85) | water (19) | CQ (1.25), DMBE (1.25) |
| 2 | Ti(O—i-Pr)$_4$ (4.4) | — | IPA (85) | water (19) | CQ (1.25), DMBE (1.25) |
| 3 | Ti(O—i-Pr)$_4$ (4.4) | Al(O—i-Pr)$_3$ (1.7) | IPA (85) | water (19) | CQ (1.25), DMBE (1.25) |
| 4 | Ti(O—i-Pr)$_4$ (4.4) | Ca(O—i-Pr)$_2$ (1.3) | IPA (85) | water (19) | CQ (1.25), DMBE (1.25) |
| 5 | Ti(O—i-Pr)$_4$ (3.1) | — | IPA (85) | water (19) | CQ (1.25), DMBE (1.25) |
| 6 | Ti(O—n-Bu)$_4$ (5.3) | — | IPA (85) | water (19) | CQ (1.25), DMBE (1.25) |
| 7 | Zr(O—i-Pr)$_4$ (5.8) | — | IPA (85) | water (19) | CQ (1.25), DMBE (1.25) |
| 8 | Ti(O—i-Pr)$_4$ (4.4) | — | acetone (85) | water (19) | CQ (1.25), DMBE (1.25) |
| 9 | Ti(O—i-Pr)$_4$ (6.8) | — | IPA (85) | water (19) | CQ (1.25), DMBE (1.25) |
| 10 | Ti(O—i-Pr)$_4$ (6.8) | — | IPA (85) | water (19) | CQ (1.25), DMBE (1.25) |

Note [1] Contains 0.03 parts by mass of BHT.

TABLE 2

| Ex. No. | Mol number per gram of polymerizable monomer (mmols/g) | | | pH of 10% ethanol solution | Durability of adhesion Adhering strength/MPa (standard deviation) | |
|---|---|---|---|---|---|---|
| | Phosphoric diester polymeriable monomer | Group IV element ions | Other metal ions | | Enamel | Dentin |
| 1 | PM2 (0.47) | Ti$^{4+}$ (0.24) | — | 2.0 | 20.1 (2.5) | 19.7 (3.6) |
| 2 | PM2 (0.47) | Ti$^{4+}$ (0.15) | — | 2.0 | 21.0 (4.1) | 21.6 (2.5) |
| 3 | PM2 (0.47) | Ti$^{4+}$ (0.15) | Al$^{3+}$ (0.08) | 2.1 | 23.2 (3.0) | 21.3 (3.9) |
| 4 | PM2 (0.47) | Ti$^{4+}$ (0.15) | Ca$^{2+}$ (0.08) | 2.1 | 20.8 (3.6) | 18.9 (4.1) |
| 5 | PM2 (0.52) | Ti$^{4+}$ (0.11) | — | 1.9 | 20.3 (3.0) | 19.3 (2.2) |
| 6 | PM2 (0.47) | Ti$^{4+}$ (0.16) | — | 2.0 | 20.2 (4.8) | 17.7 (4.1) |
| 7 | PM2 (0.47) | Zr$^{4+}$ (0.15) | — | 2.0 | 19.9 (3.0) | 16.2 (4.1) |
| 8 | PM2 (0.47) | Ti$^{4+}$ (0.15) | — | 2.0 | 20.8 (3.9) | 21.1 (2.9) |

TABLE 2-continued

| Ex. No. | Mol number per gram of polymerizable monomer (mmols/g) | | | pH of 10% ethanol solution | Durability of adhesion Adhering strength/MPa (standard deviation) | |
|---|---|---|---|---|---|---|
| | Phosphoric diester polymeriable monomer | Group IV element ions | Other metal ions | | Enamel | Dentin |
| 9 | phenyl-P (0.87) | $Ti^{4+}$ (0.24) | — | 1.9 | 18.2 (4.1) | 17.2 (2.5) |
| 10 | PM2 (0.78) | $Ti^{4+}$ (0.24) | — | 1.8 | 21.2 (2.5) | 20.3 (2.7) |

TABLE 3

| Comp. Ex. No. | Adhesive for composite resin (parts by mass)[Note 1] | |
|---|---|---|
| | Polymerizable monomer | |
| | Phosphoric diester polymerizable monomer | Other polymerizable monomers |
| 1 | PM2 (15.1) | PM1 (9.9), BisGMA (30), 3G (20), HEMA (25) |
| 2 | PM2 (15.1) | PM1 (9.9), BisGMA (30), 3G (20), HEMA (25) |
| 3 | phenyl-P (25.0) | BisGMA (30), 3G (20), HEMA (25) |
| 4 | PM2 (25.0) | BisGMA (30), 3G (20), HEMA (25) |
| 5 | PM2 (15.1) | PM1 (9.9), BisGMA (30), 3G (20), HEMA (25) |
| 6 | PM2 (15.1) | PM1 (9.9), BisGMA (30), 3G (20), HEMA (25) |
| 7 | PM2 (15.1) | PM1 (9.9), BisGMA (30), 3G (20), HEMA (25) |
| 8 | PM2 (15.1) | PM1 (9.9), BisGMA (30), 3G (20), HEMA (25) |
| 9 | PM2 (15.1) | PM1 (9.9), BisGMA (30), 3G (20), HEMA (25) |
| 10 | PM2 (15.1) | PM1 (9.9), BisGMA (30), 3G (20), HEMA (25) |
| 11 | PM2 (15.1) | PM1 (9.9), BisGMA (30), 3G (20), HEMA (25) |
| 12 | PM2 (15.1) | PM1 (9.9), BisGMA (30), 3G (20), HEMA (25) |
| 13 | PM2 (15.1) | PM1 (9.9), BisGMA (30), 3G (20), HEMA (25) |
| 14 | — | PM1 (10), BisGMA (30), 3G (20), HEMA (25) |
| 15 | PM2 (15.1) | PM1 (9.9), BisGMA (30), 3G (20), HEMA (25) |
| 16 | PM2 (15.1) | PM1 (9.9), BisGMA (30), 3G (20), HEMA (25) |

| Comp. Ex. No. | Adhesive for composite resin (parts by mass)[Note 1] | | | | |
|---|---|---|---|---|---|
| | Compounds of Group IV element ion sources | Compounds of other metal ion sources | Organic solvent | Water | Polymerization initiator |
| 1 | — | — | IPA (85) | water (19) | CQ (1.25), DMBE (1.25) |
| 2 | — | — | acetone (85) | water (19) | CQ (1.25), DMBE (1.25) |
| 3 | — | — | IPA (85) | water (19) | CQ (1.25), DMBE (1.25) |
| 4 | — | — | IPA (85) | water (19) | CQ (1.25), DMBE (1.25) |
| 5 | — | Al(O—i-Pr)$_3$ (3.1) | IPA (85) | water (19) | CQ (1.25), DMBE (1.25) |
| 6 | — | Ca(O—i-Pr)$_3$ (2.4) | IPA (85) | water (19) | CQ (1.25), DMBE (1.25) |
| 7 | — | Y(O—i-Pr)$_3$ (4.0) | IPA (85) | water (19) | CQ (1.25), DMBE (1.25) |
| 8 | — | La(O—i-Pr)$_3$ (4.7) | IPA (85) | water (19) | CQ (1.25), DMBE (1.25) |
| 9 | — | Sc(O—i-Pr)$_3$ (3.3) | IPA (85) | water (19) | CQ (1.25), DMBE (1.25) |
| 10 | — | Ce(O—i-Pr)$_4$ (5.6) | IPA (85) | water (19) | CQ (1.25), DMBE (1.25) |
| 11 | — | Yb(O—i-Pr)$_3$ (5.3) | IPA (85) | water (19) | CQ (1.25), DMBE (1.25) |
| 12 | TiO$_2$ (1.2) | — | IPA (85) | water (19) | CQ (1.25), DMBE (1.25) |
| 13 | ZrO$_2$ (1.8) | — | IPA (85) | water (19) | CQ (1.25), DMBE (1.25) |
| 14 | Ti(O—i-Pr)$_4$ (2.2) | — | IPA (85) | water (19) | CQ (1.25), DMBE (1.25) |
| 15 | Ti(O—i-Pr)$_4$ (1.2) | — | IPA (85) | water (19) | CQ (1.25), DMBE (1.25) |
| 16 | Ti(O—i-Pr)$_4$ (14.0) | — | IPA (85) | water (19) | CQ (1.25), DMBE (1.25) |

[Note 1] Contains 0.03 parts by mass of BHT.

TABLE 4

| Comp. Ex. No. | Mol number per gram of polymerizable monomer (mmols/g) | | | pH of 10% ethanol solution | Durability of adhesion Adhering strength/MPa (standard deviation) | |
|---|---|---|---|---|---|---|
| | Phosphoric diester polymeriable monomer | Group IV element ions | Other metal ions | | Enamel | Dentin |
| 1 | PM2 (0.47) | — | — | 2.0 | 4.2 (3.5) | 4.2 (2.9) |
| 2 | PM2 (0.47) | — | — | 2.0 | 3.9 (3.0) | 3.7 (2.5) |
| 3 | phenyl-P (0.87) | — | — | 1.9 | 4.1 (2.8) | 3.9 (2.5) |
| 4 | PM2 (0.78) | — | — | 1.8 | 4.2 (3.2) | 4.0 (2.1) |
| 5 | PM2 (0.47) | — | $Al^{3+}$ (0.15) | 2.2 | 16.4 (2.2) | 13.1 (3.2) |
| 6 | PM2 (0.47) | — | $Ca^{2+}$ (0.15) | 2.2 | 12.1 (3.6) | 9.5 (2.7) |
| 7 | PM2 (0.47) | — | $Y^{3+}$ (0.01) | 2.0 | 8.0 (2.1) | 6.8 (1.6) |
| 8 | PM2 (0.47) | — | $La^{3+}$ (0.04) | 2.1 | 13.1 (1.5) | 10.5 (3.1) |
| 9 | PM2 (0.47) | — | $Sc^{3+}$ (0.01) | 2.0 | 7.9 (1.2) | 4.9 (1.1) |
| 10 | PM2 (0.47) | — | $Ce^{4+}$ (0.01) | 2.0 | 9.0 (2.1) | 9.8 (3.0) |
| 11 | PM2 (0.47) | — | $Yb^{3+}$ (0.01) | 2.0 | 8.8 (1.9) | 7.2 (2.6) |
| 12 | PM2 (0.47) | $Ti^{4+}$ (0.01) | — | 2.0 | 4.6 (2.6) | 4.3 (3.1) |
| 13 | PM2 (0.47) | $Zr^{4+}$ (0.01) | — | 2.0 | 3.9 (1.7) | 3.1 (2.1) |
| 14 | — | $Ti^{4+}$ (0.08) | — | 2.0 | 10.2 (4.1) | 5.1 (1.4) |
| 15 | PM2 (0.47) | $Ti^{4+}$ (0.04) | — | 2.0 | 13.5 (3.6) | 12.8 (5.3) |
| 16 | PM2 (0.47) | $Ti^{4+}$ (0.49) | — | 2.0 | 10.5 (1.6) | 8.5 (3.3) |

In Examples 1 to 10, the phosphoric diester polymerizable monomers and ions of the element of the Group IV were so blended as to satisfy the constitution specified by the invention. In all cases, tested results of the durability of adhesion were favorable to both the enamel and the dentin.

In Comparative Examples 1 to 4 without at all containing ion of the element of the Group IV or polyvalent metal ions, the adhering strength after the durability test was not sufficient for both the enamel and the dentin. In Comparative Examples 5 to 11 that contained polyvalent metal ions other than the ions of the element of the Group IV, the adhering strength after the durability test was not sufficient for both the enamel and the dentin. In Comparative Examples 12 and 13 that used titanium oxide or zirconium oxide as the compound of the element of the Group IV, titanium ions or zirconium ions did not almost elute out, and the adhering strength after the durability test was not sufficient for both the enamel or the dentin. In Comparative Example 14 that used only the acid group-containing polymerizable monomer other than the phosphoric diester polymerizable monomer, the adhering strength after the durability test was not sufficient for both the enamel or the dentin. In Comparative Examples 15 and 16 that contained ions of the element of the Group IV but in amounts outside the range of the present invention, the adhering strength after the durability test was not sufficient for both the enamel and the dentin.

Examples 11 to 18, Comparative Examples 17 to 31

Primers of the compositions shown in Tables 5 and 7 were prepared in the same manner as the adhesive material of Example 1, and were used for two-step type adhesive materials for composite resin.

The acid group-containing polymerizable monomers and various kinds of ions contained in the primers were measured. By using the primers, adhesion test pieces were prepared according to the method of preparing the adhesion test piece II and were tested for their adhering strength to the enamel and to the dentin after the durability test. The evaluated results were as shown in Tables 6 and 8.

TABLE 5

| | Primer (parts by mass)[Note 1] | | | | |
|---|---|---|---|---|---|
| | Polymerizable monomer | | | | |
| Ex. No. | Phosphoric diester polymerizable monomer | Other polymerizable monomers | Compounds of Group IV element ion sources | Organic solvent | Water |
| 11 | PM2 (12.1) | PM1 (7.9), HEMA (80) | Ti(O—i-Pr)$_4$ (8.8) | IPA (85) | water (20) |
| 12 | PM2 (30.2) | PM1 (19.8), HEMA (80) | Ti(O—i-Pr)$_4$ (13.6) | IPA (85) | water (20) |
| 13 | PM2 (30.2) | PM1 (19.8), HEMA (50) | Zr(O—i-Pr)$_4$ (12.0) | IPA (85) | water (20) |
| 14 | PM2 (30) | HEMA (50) | Ti(O—i-Pr)$_4$ (8.8) | IPA (85) | water (20) |
| 15 | PM2 (30.2) | PM1 (19.8), HEMA (50) | Ti(O—i-Pr)$_4$ (8.8) | IPA (85) | water (20) |
| 16 | PM2 (30.2) | PM1 (19.8), HEMA (50) | Ti(O—n-Bu)$_4$ (10.6) | IPA (85) | water (20) |
| 17 | PM2 (30.2) | PM1 (19.8), BisGMA (5), HEMA (45) | Ti(O—i-Pr)$_4$ (4.4) | IPA (85) | water (20) |
| 18 | phenyl-P (30) | HEMA (50) | Ti(O—i-Pr)$_4$ (8.8) | IPA (85) | water (20) |

[Note 1] Contains 0.03 parts by mass of BHT.

TABLE 6

| Ex. No. | Phosphoric diester polymeriable monomer | Group IV element ions | pH of 10% ethanol solution | Durability of adhesion Adhering strength/MPa (standard deviation) | |
|---|---|---|---|---|---|
| | Mol number per gram of polymerizable monomer (mmols/g) | | | | |
| | | | | Enamel | Dentin |
| 11 | PM2 (0.38) | Ti$^{4+}$ (0.31) | 1.6 | 17.5 (2.1) | 15.1 (3.6) |
| 12 | PM2 (0.94) | Ti$^{4+}$ (0.48) | 1.6 | 21.0 (4.1) | 19.8 (2.5) |
| 13 | PM2 (0.94) | Zr$^{4+}$ (0.31) | 1.6 | 17.7 (1.8) | 15.7 (2.1) |
| 14 | PM2 (1.16) | Ti$^{4+}$ (0.39) | 1.4 | 19.2 (2.1) | 18.1 (1.7) |
| 15 | PM2 (0.94) | Ti$^{4+}$ (0.31) | 1.6 | 20.9 (2.9) | 19.3 (3.7) |
| 16 | PM2 (0.94) | Ti$^{4+}$ (0.31) | 1.6 | 19.7 (3.9) | 18.1 (2.1) |
| 17 | PM2 (0.94) | Ti$^{4+}$ (0.15) | 1.6 | 19.5 (1.9) | 18.5 (3.0) |
| 18 | phenyl-P (1.31) | Ti$^{4+}$ (0.39) | 1.5 | 17.0 (2.8) | 16.1 (1.7) |

Examples 11 to 18 were concerned to dentin primers in which the components were so blended together as to satisfy the constitution specified by the invention. In all cases, favorable durability was obtained maintaining good adhering strength to both the enamel and the dentin.

Comparative Examples 17 to 21 contained no ion of the element of the Group IV or contained ions of the element of the Group IV but in amounts outside the range of the present invention. The adhering strength after the durability test was not sufficient for both the enamel and the dentin. In Comparative Examples 22 and 23 that used titanium oxide or zirconium oxide as the compound of the element of the Group IV, titanium ions or zirconium ions did not almost elute out, and the adhering strength after the durability test was not sufficient for both the enamel and the dentin. In Comparative Example 24 that used only the acid group-containing polymerizable monomer other than the phosphoric diester polymerizable monomer, the adhering strength after the durability

TABLE 7

| Comp. Ex. No. | Primer (parts by mass)$^{Note\ 1}$ | | | | | |
|---|---|---|---|---|---|---|
| | Polymerizable monomer | | Compounds of | | | |
| | (*) | Other polymerizable monomers | Group IV element ion sources | Compounds of other metal ion sources | Organic solvent | Water |
| 17 | PM2 (30.2) | PM1 (19.8), HEMA (50) | — | — | IPA (85) | water (20) |
| 18 | PM2 (30) | HEMA (50) | — | — | IPA (85) | water (20) |
| 19 | phenyl-P (30) | HEMA (50) | — | — | IPA (85) | water (20) |
| 20 | PM2 (30.2) | PM1 (19.8), HEMA (50) | Ti(O—i-Pr)$_4$ (2.4) | — | IPA (85) | water (20) |
| 21 | PM2 (30.2) | PM1 (19.8), HEMA (50) | Ti(O—i-Pr)$_4$ (28.0) | — | IPA (85) | water (20) |
| 22 | PM2 (30.2) | PM1 (19.8), HEMA (50) | TiO$_2$ (2.4) | — | IPA (85) | water (20) |
| 23 | PM2 (30.2) | PM1 (19.8), HEMA (50) | ZrO$_2$ (3.6) | — | IPA (85) | water (20) |
| 24 | — | PM1 (20), HEMA (50) | Ti(O—i-Pr)$_4$ (4.4) | — | IPA (85) | water (20) |
| 25 | PM2 (30.2) | PM1 (19.8), HEMA (50) | — | Al(O—i-Pr)$_3$ (6.3) | IPA (85) | water (20) |
| 26 | PM2 (30.2) | PM1 (19.8), HEMA (50) | — | Ca(O—i-Pr)$_2$ (4.9) | IPA (85) | water (20) |
| 27 | PM2 (30.2) | PM1 (19.8), HEMA (50) | — | Y(O—i-Pr)$_3$ (8.3) | IPA (85) | water (20) |
| 28 | PM2 (30.2) | PM1 (19.8), HEMA (50) | — | La(O—i-Pr)$_3$ (9.8) | IPA (85) | water (20) |
| 29 | PM2 (30.2) | PM1 (19.8), HEMA (50) | — | Sc(O—i-Pr)$_3$ (6.9) | IPA (85) | water (20) |
| 30 | PM2 (30.2) | PM1 (19.8), HEMA (50) | — | Ce(O—i-Pr)$_4$ (11.7) | IPA (85) | water (20) |
| 31 | PM2 (30.2) | PM1 (19.8), HEMA (50) | — | Yb(O—i-Pr)$_3$ (10.9) | IPA (85) | water (20) |

$^{Note\ 1}$Contains 0.03 parts by mass of BHT.
(*): Phosphoric diester polymerizable monomer

TABLE 8

| Comp. Ex. No. | Mol number per gram of polymerizable monomer (mmols/g) | | | pH of 10% ethanol solution | Durability of adhesion Adhering strength/MPa (standard deviation) | |
|---|---|---|---|---|---|---|
| | Phosphoric diester polymeriable monomer | Group IV element ions | Other metal ions | | Enamel | Dentin |
| 17 | PM2 (0.94) | — | — | 1.6 | 4.2 (2.8) | 4.8 (2.5) |
| 18 | PM2 (1.16) | — | — | 1.4 | 3.6 (2.1) | 3.9 (2.2) |
| 19 | phenyl-P (1.31) | — | — | 1.5 | 3.4 (1.9) | 3.7 (1.7) |
| 20 | PM2 (0.94) | Ti$^{4+}$ (0.08) | — | 1.6 | 13.2 (3.4) | 10.1 (3.7) |
| 21 | PM2 (0.94) | Ti$^{4+}$ (0.99) | — | 1.6 | 13.1 (2.6) | 9.0 (2.3) |
| 22 | PM2 (0.94) | Ti$^{4+}$ (0.01) | — | 1.6 | 10.5 (3.4) | 7.3 (3.4) |
| 23 | PM2 (0.94) | Zr$^{4+}$ (0.01) | — | 1.6 | 10.2 (3.1) | 6.9 (2.3) |
| 24 | — | Ti$^{4+}$ (0.22) | — | 1.4 | 9.8 (2.8) | 5.3 (1.9) |
| 25 | PM2 (0.94) | — | Al$^{3+}$ (0.31) | 1.8 | 17.0 (2.7) | 12.0 (3.7) |
| 26 | PM2 (0.94) | — | Ca$^{2+}$ (0.31) | 1.8 | 17.1 (3.6) | 8.8 (2.3) |
| 27 | PM2 (0.94) | — | Y$^{3+}$ (0.01) | 1.6 | 5.1 (1.7) | 3.9 (2.0) |
| 28 | PM2 (0.94) | — | La$^{3+}$ (0.05) | 1.7 | 14.9 (2.0) | 10.9 (1.4) |
| 29 | PM2 (0.94) | — | Sc$^{3+}$ (0.01) | 1.6 | 4.7 (1.3) | 4.1 (2.2) |
| 30 | PM2 (0.94) | — | Ce$^{4+}$ (0.01) | 1.6 | 8.0 (1.5) | 5.0 (2.0) |
| 31 | PM2 (0.94) | — | Yb$^{3+}$ (0.01) | 1.6 | 6.1 (2.7) | 3.9 (2.2) | test was not sufficient for both the enamel and the dentin. In Comparative Examples 25 to 31 that contained polyvalent metal ions other than the ions of the element of the Group IV, the adhering strength after the durability test was not sufficient for both the enamel and the dentin.

Example 19

25.0 Grams of an equimolar mixture of PM1 and PM2, 30 g of BisGMA, 20 g of 3G and 25 g of HEMA as polymerizable monomers; 4.4 g of titanium isopropoxide as a source of titanium ions; 1.25 g of camphorquinone, 1.25 g of DMBE and 85 g of IPA as polymerization initiators; and 0.25 g of BHT, 0.19 g of HQME and 9.8 g of hydrophobic fumed silica having an average particle diameter of 0.01 μm as other components, were mixed and stirred together until it became homogeneous to thereby obtain a two-step type adhesive material for composite resin.

The adhesive material was measured for its phosphoric acid type polymerizable monomer and metal ions. By using the adhesive material, an adhesion test piece was prepared according to the method of preparing the adhesion test piece III and was tested for its durability of adhesion to the enamel and to the dentin. The composition of the adhesive material was as shown in Table 9 and the evaluated results were as shown in Table 10.

Examples 20 to 25

Adhesive materials of different compositions shown in Table 9 were prepared in accordance with the method of Example 19. The obtained two-step type adhesive materials for composite resin were measured for their phosphoric acid type polymerizable monomers and metal ions. By using these adhesive materials, adhesion test pieces were prepared according to the method of preparing the adhesion test piece III and were tested for their durability of adhesion to the enamel and to the dentin. The compositions of the adhesive materials were as shown in Table 9 and the results were as shown in Table 10.

Comparative Examples 32 to 45

Adhesive materials of different compositions were prepared in accordance with the method of Example 19. The obtained two-step type adhesive materials for composite resin were measured for their phosphoric acid type polymerizable monomers, metal ions and pHs. By using these adhesive materials, adhesion test pieces were prepared according to the method of preparing the adhesion test piece III and were tested for their durability of adhesion to the enamel and to the dentin. The compositions of the adhesive materials were as shown in Table 11 and the results were as shown in Table 12.

TABLE 9

Adhesive for composite resin (parts by mass)[Note 1]

| | Polymerizable monomer | | | |
|---|---|---|---|---|
| Ex. No. | Phosphoric diester polymerizable monomer | Other polymerizable monomers | Compounds of Group IV element ion sources | Compounds of other metal ion sources |
| 19 | PM2 (15.1) | PM1 (9.9), BisGMA (30), 3G (20), HEMA (25) | Ti(O—i-Pr)$_4$ (6.8) | CQ (1.25), DMBE (1.25) |
| 20 | PM2 (15.1) | PM1 (9.9), BisGMA (30), 3G (20), HEMA (25) | Ti(O—i-Pr)$_4$ (4.4) | CQ (1.25), DMBE (1.25) |
| 21 | PM2 (15.1) | PM1 (9.9), BisGMA (30), 3G (20), HEMA (25) | Ti(O—i-Pr)$_4$ (3.1) | CQ (1.25), DMBE (1.25) |
| 22 | PM2 (15.1) | PM1 (9.9), BisGMA (30), 3G (20), HEMA (25) | Ti(O—n-Bu)$_4$ (5.3) | CQ (1.25), DMBE (1.25) |
| 23 | PM2 (15.1) | PM1 (9.9), BisGMA (30), 3G (20), HEMA (25) | Zr(O—i-Pr)$_4$ (5.8) | CQ (1.25), DMBE (1.25) |
| 24 | PM2 (25.0) | BisGMA (30), 3G (20), HEMA (25) | Ti(O—i-Pr)$_4$ (6.8) | CQ (1.25), DMBE (1.25) |
| 25 | phenyl-P (25.0) | BisGMA (30), 3G (20), HEMA (25) | Ti(O—i-Pr)$_4$ (6.8) | CQ (1.25), DMBE (1.25) |

[Note 1] Contains 0.03 parts by mass of BHT.

TABLE 10

| | Mol number per gram of polymerizable monomer (mmols/g) | | Durability of adhesion Adhering strength/MPa (standard deviation) | |
|---|---|---|---|---|
| Ex. No. | Phosphoric diester polymeriable monomer | Group IV element ions | Enamel | Dentin |
| 19 | PM2 (0.47) | Ti$^{4+}$ (0.24) | 21.1 (2.5) | 20.1 (3.0) |
| 20 | PM2 (0.47) | Ti$^{4+}$ (0.15) | 21.2 (2.1) | 19.9 (2.1) |
| 21 | PM2 (0.47) | Ti$^{4+}$ (0.11) | 20.8 (2.3) | 19.0 (1.9) |
| 22 | PM2 (0.47) | Ti$^{4+}$ (0.16) | 19.1 (2.2) | 18.2 (2.5) |
| 23 | PM2 (0.47) | Zr$^{4+}$ (0.15) | 18.9 (1.4) | 16.9 (2.1) |
| 24 | PM2 (0.78) | Ti$^{4+}$ (0.24) | 21.1 (2.5) | 20.1 (3.0) |
| 25 | phenyl-P (0.87) | Ti$^{4+}$ (0.24) | 21.1 (2.5) | 20.1 (3.0) |

TABLE 11

Adhesive for composite resin (parts by mass)[Note 1]
Polymerizable monomer

| Comp. Ex. No. | Phosphoric diester polymerizable monomer | Other polymerizable monomers |
|---|---|---|
| 32 | PM2 (15.1) | PM1 (9.9), BisGMA (30), 3G (20), HEMA (25) |
| 33 | PM2 (25.0) | BisGMA (30), 3G (20), HEMA (25) |
| 34 | phenyl-P (25.0) | BisGMA (30), 3G (20), HEMA (25) |
| 35 | PM2 (15.1) | PM1 (9.9), BisGMA (30), 3G (20), HEMA (25) |
| 36 | PM2 (15.1) | PM1 (9.9), BisGMA (30), 3G (20), HEMA (25) |
| 37 | PM2 (15.1) | PM1 (9.9), BisGMA (30), 3G (20), HEMA (25) |
| 38 | PM2 (15.1) | PM1 (9.9), BisGMA (30), 3G (20), HEMA (25) |
| 39 | — | PM1 (10), BisGMA (30), 3G (20), HEMA (25) |
| 40 | PM2 (15.1) | PM1 (9.9), BisGMA (30), 3G (20), HEMA (25) |
| 41 | PM2 (15.1) | PM1 (9.9), BisGMA (30), 3G (20), HEMA (25) |
| 42 | PM2 (15.1) | PM1 (9.9), BisGMA (30), 3G (20), HEMA (25) |
| 43 | PM2 (15.1) | PM1 (9.9), BisGMA (30), 3G (20), HEMA (25) |
| 44 | PM2 (15.1) | PM1 (9.9), BisGMA (30), 3G (20), HEMA (25) |
| 45 | PM2 (15.1) | PM1 (9.9), BisGMA (30), 3G (20), HEMA (25) |
| 46 | PM2 (15.1) | PM1 (9.9), BisGMA (30), 3G (20), HEMA (25) |

Adhesive for composite resin (parts by mass)[Note 1]

| Comp. Ex. No. | Compounds of Group IV element ion sources | Compounds of other metal ion sources | Polymerization initiator |
|---|---|---|---|
| 32 | — | — | CQ (1.25), DMBE (1.25) |
| 33 | — | — | CQ (1.25), DMBE (1.25) |
| 34 | — | — | CQ (1.25), DMBE (1.25) |
| 35 | Ti(O—i-Pr)$_4$ (1.2) | — | CQ (1.25), DMBE (1.25) |
| 36 | Ti(O—i-Pr)$_4$ (14.0) | — | CQ (1.25), DMBE (1.25) |
| 37 | TiO$_2$ (1.2) | — | CQ (1.25), DMBE (1.25) |
| 38 | ZrO$_2$ (1.8) | — | CQ (1.25), DMBE (1.25) |
| 39 | Ti(O—i-Pr)$_4$ (2.2) | — | CQ (1.25), DMBE (1.25) |
| 40 | — | Al(O—i-Pr)$_3$ (3.1) | CQ (1.25), DMBE (1.25) |
| 41 | — | Ca(O—i-Pr)$_2$ (2.4) | CQ (1.25), DMBE (1.25) |
| 42 | — | Y(O—i-Pr)$_3$ (4.0) | CQ (1.25), DMBE (1.25) |
| 43 | — | La(O—i-Pr)$_3$ (4.7) | CQ (1.25), DMBE (1.25) |
| 44 | — | Sc(O—i-Pr)$_3$ (3.3) | CQ (1.25), DMBE (1.25) |
| 45 | — | Ce(O—i-Pr)$_4$ (5.6) | CQ (1.25), DMBE (1.25) |
| 46 | — | Yb(O—i-Pr)$_3$ (5.3) | CQ (1.25), DMBE (1.25) |

[Note 1] Contains 0.03 parts by mass of BHT.

TABLE 12

| Comp. Ex. No. | Mol number per gram of polymerizable monomer (mmols/g) | | | Durability of adhesion Adhering strength/MPa (standard deviation) | |
|---|---|---|---|---|---|
| | Phosphoric diester polymeriable monomer | Group IV element ions | Other metal ions | Enamel | Dentin |
| 32 | PM2 (0.47) | — | — | 10.2 (2.1) | 8.9 (1.1) |
| 33 | PM2 (0.78) | — | — | 9.8 (1.6) | 8.3 (1.0) |
| 34 | phenyl-P (0.87) | — | — | 7.5 (1.3) | 7.4 (0.8) |
| 35 | PM2 (0.47) | Ti$^{4+}$ (0.04) | — | 13.8 (2.7) | 14.1 (2.3) |
| 36 | PM2 (0.47) | Ti$^{4+}$ (0.49) | — | 14.9 (1.5) | 11.2 (2.3) |
| 37 | PM2 (0.47) | Ti$^{4+}$ (0.01) | — | 14.9 (2.6) | 12.9 (1.2) |
| 38 | PM2 (0.47) | Zr$^{4+}$ (0.01) | — | 13.7 (1.3) | 13.2 (1.1) |
| 39 | — | Ti$^{4+}$ (0.08) | — | 14.2 (2.6) | 12.4 (1.0) |
| 40 | PM2 (0.47) | — | Al$^{3+}$ (0.15) | 15.5 (1.9) | 11.5 (2.7) |
| 41 | PM2 (0.47) | — | Ca$^{2+}$ (0.15) | 18.0 (2.9) | 9.2 (1.9) |
| 42 | PM2 (0.47) | — | Y$^{3+}$ (0.01) | 8.1 (1.4) | 3.1 (0.9) |
| 43 | PM2 (0.47) | — | La$^{3+}$ (0.05) | 14.4 (1.7) | 9.9 (1.0) |
| 44 | PM2 (0.47) | — | Sc$^{3+}$ (0.01) | 6.1 (1.3) | 4.9 (1.9) |
| 45 | PM2 (0.47) | — | Ce$^{4+}$ (0.01) | 7.8 (2.4) | 6.8 (1.8) |
| 46 | PM2 (0.47) | — | Yb$^{3+}$ (0.01) | 5.7 (2.4) | 5.9 (1.1) |

Examples 19 to 25 were concerned to adhesive materials in which the components were so blended together as to satisfy the constitution specified by the invention. In all cases, favorable durability was obtained maintaining good adhering strength to both the enamel and the dentin.

Comparative Examples 32 to 36 contained no ion of the element of the Group IV or contained ions of the element of the Group IV but in amounts outside the range of the present invention. The adhering strength after the durability test was not sufficient for both the enamel and the dentin. In Comparative Examples 37 and 38 that used titanium oxide or zirconium oxide as the compound of the element of the Group IV, titanium ions or zirconium ions did not almost elute out, and the adhering strength after the durability test was not sufficient for both the enamel and the dentin. In Comparative Example 39 that used only the acid group-containing polymerizable monomer other than the phosphoric diester polymerizable monomer, the adhering strength after the durability test was not sufficient for both the enamel and the dentin. In Comparative Examples 40 to 46 that contained polyvalent metal ions other than the ions of the element of the Group IV, the adhering strength after the durability test was not sufficient for both the enamel and the dentin.

Example 26

0.06 Grams of CQ, 0.1 g of DMBE, 0.1 g of perocta H, 0.2 g of BS110, 0.002 g of HQME and 0.015 g of BHT were added to 5.7 g of BisGMA, 3.8 g of 3G and 0.5 g of 14G, and the mixture was stirred in a dark place until it became homogeneous to thereby prepare a matrix thereof. 3.3 Grams of the thus obtained matrix was mixed with 6.23 g of F1 and 0.47 g of MF in an agate mortar, and the mixture was defoamed in vacuum to obtain a photocurable composite resin CR1 having a filler-filling ratio of 67.0%.

44.0 Grams of an equimolar mixture of PM1 and PM2, 7.2 g of BisGMA, 4.8 g of 3G and 44 g of HEMA as polymerizable monomers; 10.0 g of titanium isopropoxide as a source of titanium ions; and 0.75 g of BMOV, 0.14 g of BHT, 300 g of acetone and 27 g of F2 as polymerization initiators, were mixed and stirred together until the mixture became homogeneous. Thereafter, 33 g of distilled water was added thereto, and the mixture was mixed and stirred again until it became homogeneous to thereby obtain a primer comprising the adhesive composition of the invention for composite resin.

The primer was measured for its phosphoric acid type polymerizable monomer, metal ions and pH. By using the above composite resin CR1 and the primer that was prepared, an adhesion test piece was prepared according to the method of preparing the adhesion test piece IV and was tested for its durability of adhesion to the enamel and to the dentin. The composition of the adhesive material was as shown in Table 13 and the evaluated results were as shown in Table 14.

Examples 27 to 30 and Comparative Examples 47 and 48

Primers for composite resin having compositions shown in Table 13 were prepared in accordance with the method of Example 26. When NaF was to be added, an aqueous solution of a predetermined concentration was prepared in advance and was finally added together with water. By using the above composite resin CR1 and the primer that was prepared, adhesion test pieces were prepared according to the method of preparing the adhesion test piece IV and were tested for their durability of adhesion to the enamel and to the dentin. The compositions of the adhesive materials were as shown in Table 13 and the evaluated results were as shown in Table 14.

TABLE 13

| | Primer (parts by mass)[Note 1] | | | | | |
|---|---|---|---|---|---|---|
| | Polymerizable monomer | | Compounds of | | | |
| Ex. No. | (*2) | Other polymerizable monomers | metal ion sources | Organic solvent | Water | Others |
| 26 | PM2 (26.6) | PM1 (17.4), BisGMA (7.2), 3G (4.8), HEMA (44) | Ti(O—i-Pr)$_4$ (10.0) | (*3) | (*4) | BMOV (0.75) |
| 27 | PM2 (26.6) | PM1 (17.4), BisGMA (7.2), 3G (4.8), HEMA (44) | Ti(O—i-Pr)$_4$ (10.0) | (*3) | (*4) | BMOV (0.75) NaF (0.8) |
| 28 | PM2 (26.6) | PM1 (17.4), BisGMA (7.2), 3G (4.8), HEMA (44) | Ti(O—i-Pr)$_4$ (8.6) TiF$_4$ (0.6) | (*3) | (*4) | BMOV (0.75) NaF (0.8) |
| 29 | PM2 (26.6) | PM1 (17.4), BisGMA (7.2), 3G (4.8), HEMA (44) | Ti(O—i-Pr)$_4$ (8.6) TiF$_4$ (0.6) | (*3) | (*4) | BMOV (0.75) |
| 30 | PM2 (26.6) | PM1 (17.4), BisGMA (7.2), 3G (4.8), HEMA (44) | Ti(O—i-Pr)$_4$ (10.0) | (*3) | (*4) | BMOV (0.75) NaF (0.8), CQ (0.1) |
| 47 (*1) | PM2 (26.6) | PM1 (17.4), BisGMA (7.2), 3G (4.8), HEMA (44) | Al(O—i-Pr)$_3$ (9.7) | (*3) | (*4) | BMOV (0.75) |
| 48 (*1) | PM2 (26.6) | PM1 (17.4), BisGMA (7.2), 3G (4.8), HEMA (44) | Ca(O—i-Pr)$_2$ (11.1) | (*3) | (*4) | BMOV (0.75) |

Note [1]Contains 0.14 parts by mass of BHT and 27 parts by mass of F2.

(*1): Comp. Ex. No.

(*2): Phosphoric diester polymerizable monomer (*3): acetone (300)

(*4): water (33)

TABLE 14

| | Mol number per gram of polymerizable monomer (mmols/g) | | | pH of 10% ethanol solution | White precipitation after stored at 25° C. for 90 days | Durability of adhesion Adhering strength/MPa (standard deviation) | |
|---|---|---|---|---|---|---|---|
| Ex. No. | Phosphoric diester polymeriable monomer | Metal ion | F− ion | | | Enamel | Dentin |
| 26 | PM2 (0.83) | Ti$^{4+}$ (0.35) | | 1.6 | X | 19.2 (3.3) | 17.1 (2.8) |
| 27 | PM2 (0.83) | Ti$^{4+}$ (0.35) | 0.19 | 1.8 | ◯ | 19.3 (2.3) | 17.3 (3.7) |
| 28 | PM2 (0.83) | Ti$^{4+}$ (0.35) | 0.38 | 1.8 | ◯ | 19.1 (3.6) | 17.6 (4.1) |
| 29 | PM2 (0.83) | Ti$^{4+}$ (0.35) | 0.19 | 1.6 | ◯ | 19.7 (3.1) | 17.8 (4.3) |
| 30 | PM2 (0.83) | Ti$^{4+}$ (0.35) | 0.19 | 1.8 | ◯ | 20.7 (2.9) | 19.1 (2.5) |
| 47* | PM2 (0.83) | Al$^{3+}$ (0.47) | | 1.8 | — | 17.9 (3.9) | 15.3 (3.3) |
| 48* | PM2 (0.83) | Ca$^{2+}$ (0.70) | | 1.8 | — | 12.7 (3.9) | 10.1 (2.1) |

*Comp. Ex. No.

Examples 26 to 30 were concerned to primers in which the components were so blended together as to satisfy the constitution specified by the invention. In all cases, favorable durability was obtained maintaining good adhering strength to both the enamel and the dentin. Examples 27 to 30 were concerned to primers containing fluoride ions in addition to ions of the element of the Group IV. There was no white precipitation even after the primers were stored at 25° C. for 90 days. Similarly, Comparative Examples 47 and 48 were concerned to primers containing metal ions other than the ions of the element of the Group IV. The results of durability test proved no good durability of adhesion.

The invention claimed is:

1. A dental adhesive composition containing:
   (A) a polymerizable monomer that contains not less than 10 mass % of a polymerizable monomer (A-1) that has a hydrogenphosphate diester group; and
   (B) ions of an element of the Group IV;
   wherein the content of the ions of the element of the Group IV is 0.1 to 1.0 in terms of a mole ratio to the hydrogenphosphate diester groups of the polymerizable monomer (A-1) that has the hydrogenphosphate diester group;
   wherein ions (B) of the element of the Group IV are polyvalent ions having a valence of 4 or more eluted out from a source of a metal alkoxide of the element of the Group IV; and
   wherein the composition further comprises water (E).

2. The dental adhesive composition according to claim 1, wherein ions of the element of the Group IV are titanium ions.

3. The dental adhesive composition according to claim 1, wherein a polymerization initiator (C) is, further, contained.

4. The dental adhesive composition according to claim 1, wherein the composition is acidic.

5. The dental adhesive composition according to claim 1, wherein fluoride ions (D) are, further, contained at a molar ratio of 0.4 to 4.0 to the ions of the element of the Group IV.

6. A method of producing a dental adhesive composition by mixing together:
   (A) a polymerizable monomer that contains not less than 10 mass % of a polymerizable monomer (A-1) that has a hydrogenphosphate diester group;
   (E) water; and
   (B$_{alk}$) a metal alkoxide of an element of the Group IV in such an amount that the amount of ions of the element of the Group IV is 0.1 to 1.0 in terms of a mole ratio to the hydrogenphosphate diester groups of the polymerizable monomer (A-1) that has the hydrogenphosphate diester group;
   wherein the polymerizable monomer (A-1) that has the hydrogenphosphate diester group is mixed to the metal alkoxide of the element of the Group IV (B$_{alk}$), first, and is, thereafter, mixed to water (E);
   wherein ions (B) of the element of the Group IV are polyvalent ions having a valence of 4 or more eluted out from a source of a metal alkoxide of the element of the Group IV.

* * * * *